(12) United States Patent
Choi et al.

(10) Patent No.: US 8,808,941 B2
(45) Date of Patent: Aug. 19, 2014

(54) NAPHTHOXAZINE BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

(75) Inventors: Seongwoo Choi, Yongin-si (KR); Jungock Park, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 6 days.

(21) Appl. No.: 13/466,843

(22) Filed: May 8, 2012

(65) Prior Publication Data

US 2012/0219877 A1     Aug. 30, 2012

Related U.S. Application Data

(62) Division of application No. 12/262,854, filed on Oct. 31, 2008, now Pat. No. 8,188,210.

(30) Foreign Application Priority Data

Nov. 2, 2007   (KR) .......................... 10-2007-0111587
Oct. 9, 2008   (KR) .......................... 10-2008-0099351

(51) Int. Cl.
  *H01M 8/10*    (2006.01)
  *H01M 4/86*    (2006.01)
  *H01M 4/92*    (2006.01)
  *C08G 73/06*   (2006.01)
  *C07D 498/04*  (2006.01)

(52) U.S. Cl.
  CPC ............ *C07D 498/04* (2013.01); *H01M 8/103* (2013.01); *H01M 8/1048* (2013.01); *C08G 73/06* (2013.01); *H01M 4/926* (2013.01); *H01M 8/1039* (2013.01); *H01M 2300/0082* (2013.01); *H01M 4/921* (2013.01); *Y02E 60/521* (2013.01); *H01M 8/1027* (2013.01)
  USPC ............ 429/482; 429/492; 429/524; 429/531

(58) Field of Classification Search
  None
  See application file for complete search history.

(56) References Cited

U.S. PATENT DOCUMENTS

| | | |
|---|---|---|
| 4,828,699 A | 5/1989 | Soehngen |
| 5,098,985 A | 3/1992 | Harris et al. |
| 5,250,633 A | 10/1993 | Calundann et al. |
| 5,410,012 A | 4/1995 | Connell et al. |
| 5,525,436 A | 6/1996 | Savinell et al. |
| 5,637,670 A | 6/1997 | Connell et al. |
| 5,945,233 A | 8/1999 | Onorato et al. |
| 6,042,968 A | 3/2000 | Onorato et al. |
| 6,482,946 B1 | 11/2002 | Dettloff et al. |
| 6,620,905 B1 | 9/2003 | Musa |
| 6,855,674 B2 | 2/2005 | Gutierrez |
| 7,094,490 B2 | 8/2006 | Cao et al. |
| 7,157,509 B2 | 1/2007 | Li et al. |
| 7,371,480 B2 | 5/2008 | Ono et al. |
| 7,388,035 B2 | 6/2008 | Kim et al. |
| 7,405,021 B2 | 7/2008 | Gascoyne et al. |
| 7,510,678 B2 | 3/2009 | Kim et al. |
| 7,619,044 B2 | 11/2009 | Lee et al. |
| 7,649,025 B2 | 1/2010 | Kitamura et al. |
| 7,709,579 B2 | 5/2010 | Lehmann et al. |
| 2001/0041283 A1 | 11/2001 | Hitomi |
| 2002/0127474 A1 | 9/2002 | Fleischer et al. |
| 2002/0164516 A1 | 11/2002 | Hasegawa et al. |
| 2003/0190516 A1 | 10/2003 | Tanno |
| 2004/0005493 A1 | 1/2004 | Tanno |
| 2004/0028976 A1 | 2/2004 | Cabasso et al. |
| 2004/0206953 A1 | 10/2004 | Morena et al. |
| 2004/0231143 A1 | 11/2004 | Visco et al. |
| 2004/0241522 A1 | 12/2004 | Ono et al. |
| 2004/0261660 A1 | 12/2004 | Li et al. |
| 2005/0074651 A1 | 4/2005 | Kidai et al. |
| 2005/0084728 A1 | 4/2005 | Kim et al. |
| 2005/0089744 A1 | 4/2005 | Kim et al. |
| 2005/0130006 A1 | 6/2005 | Hoshi et al. |
| 2005/0142413 A1 | 6/2005 | Kimura et al. |
| 2005/0247908 A1 | 11/2005 | Keller et al. |
| 2006/0078774 A1 | 4/2006 | Uensal et al. |
| 2006/0241192 A1 | 10/2006 | Kitamura et al. |
| 2007/0020507 A1 | 1/2007 | Kim et al. |

| | | | |
|---|---|---|---|
| 2007/0141426 | A1 | 6/2007 | Choi et al. |
| 2007/0184323 | A1 | 8/2007 | Lee et al. |
| 2007/0200994 | A1 | 8/2007 | Yanagisawa |
| 2007/0238723 | A1 | 10/2007 | Goble et al. |
| 2007/0275285 | A1 | 11/2007 | Choi et al. |
| 2008/0020264 | A1 | 1/2008 | Sun et al. |
| 2008/0045688 | A1 | 2/2008 | Lin et al. |
| 2008/0050633 | A1 | 2/2008 | Kwon et al. |
| 2008/0118817 | A1 | 5/2008 | Lee et al. |
| 2008/0145743 | A1 | 6/2008 | Choi et al. |
| 2008/0157422 | A1 | 7/2008 | Lee et al. |
| 2009/0075147 | A1 | 3/2009 | Kitamura et al. |
| 2009/0117436 | A1 | 5/2009 | Choi et al. |
| 2009/0117440 | A1 | 5/2009 | Choi et al. |
| 2010/0273087 | A1 | 10/2010 | Choi et al. |
| 2011/0189581 | A1 | 8/2011 | Choi et al. |

FOREIGN PATENT DOCUMENTS

| | | | |
|---|---|---|---|
| CN | 101220153 | 7/2008 | |
| DE | 2034 887 | 1/1972 | |
| DE | 603 02 673 | 8/2006 | |
| EP | 1 247 844 | 10/2002 | |
| EP | 1 253 661 | 10/2002 | |
| EP | 1 760 110 | 3/2007 | |
| EP | 1 881 549 | 1/2008 | |
| JP | 10-25343 | 1/1998 | |
| JP | 11-503262 | 3/1999 | |
| JP | 11-97011 | 4/1999 | |
| JP | 2001-19844 | 1/2001 | |
| JP | 2001-270891 | 10/2001 | |
| JP | 2001-271070 | 10/2001 | |
| JP | 2002-260682 | 9/2002 | |
| JP | 2003-12747 | 1/2003 | |
| JP | 2003-12924 | 1/2003 | |
| JP | 2003-286320 | 10/2003 | |
| JP | 2003-327694 | 11/2003 | |
| JP | 2004-43547 | 2/2004 | |
| JP | 2004-103494 | 4/2004 | |
| JP | 2004-149779 | 5/2004 | |
| JP | 2004-179514 | 6/2004 | |
| JP | 2005-41936 | 2/2005 | |
| JP | 2005-82690 | 3/2005 | |
| JP | 2005-283082 | 10/2005 | |
| JP | 2006-339065 | 12/2006 | |
| JP | 2007-70631 | 3/2007 | |
| JP | 2007-214108 | 8/2007 | |
| JP | 2007-231041 | * 9/2007 | ............... C08F 38/00 |
| KR | 10-2006-0011831 | 2/2006 | |
| KR | 10-2006-0055291 | 5/2006 | |
| KR | 10-2007-0025626 | 3/2007 | |
| KR | 10-2007-0025627 | 3/2007 | |
| KR | 10-0745741 | 7/2007 | |
| KR | 10-2007-0102579 | 10/2007 | |
| WO | WO 96/13872 | 5/1996 | |
| WO | WO 02/14334 | 2/2002 | |
| WO | WO 02/057279 | 7/2002 | |
| WO | WO 03/072638 | 9/2003 | |
| WO | WO 2004/009708 | 1/2004 | |
| WO | WO 2004/101509 | 11/2004 | |
| WO | WO 2005/000955 | 1/2005 | |
| WO | WO 2006/132207 | 12/2006 | |

OTHER PUBLICATIONS

Machine translation of JP 2007-231041, obtained from <http://dossier.ipdl.inpit.go.jp/text_trans.html>, Accessed on Apr. 20, 2013.*
U.S. Office Action dated Jun. 22, 2009, issued in corresponding U.S. Appl. No. 11/947,011.
U.S. Office Action dated Sep. 3, 2009, issued in corresponding U.S. Appl. No. 11/743,778.
U.S. Office Action dated Sep. 8, 2009, issued in corresponding U.S. Appl. No. 11/765,033.
U.S. Office Action dated Jun. 1, 2010, issued in corresponding U.S. Appl. No. 11/765,056.
U.S. Office Action dated Jan. 8, 2010, issued in corresponding U.S. Appl. No. 11/514,254.
U.S. Office Action dated Jan. 15, 2010, issued in corresponding U.S. Appl. No. 11/947,011.
U.S. Office Action dated Feb. 19, 2010, issued in corresponding U.S. Appl. No. 11/743,778.
U.S. Office Action dated Mar. 30, 2010, issued in corresponding U.S. Appl. No. 11/947,011.
U.S. Office Action dated May 6, 2010, issued in corresponding U.S. Appl. No. 11/514,254.
U.S. Office Action dated Jun. 17, 2010, issued in corresponding U.S. Appl. No. 11/765,033.
U.S. Office Action dated Jul. 11, 2011, issued in corresponding U.S. Appl. No. 12/208,492.
U.S. Office Action dated Aug. 11, 2011, issued in corresponding U.S. Appl. No. 12/247,338.
U.S. Office Action dated Aug. 18, 2011, issued in corresponding U.S. Appl. No. 12/266,039.
U.S. Office Action dated Sep. 2, 2011, issued in corresponding U.S. Appl. No. 12/262,854.
U.S. Office Action dated Sep. 12, 2011, issued in corresponding U.S. Appl. No. 12/263,011.
U.S. Office Action dated Nov. 14, 2011, issued in corresponding U.S. Appl. No. 12/208,492.
U.S. Office Action dated Dec. 12, 2011, issued in corresponding U.S. Appl. No. 12/263,011.
U.S. Office Action dated Dec. 22, 2011, issued in corresponding U.S. Appl. No. 12/247,338.
U.S. Office Action dated Jan. 20, 2012, issued in corresponding U.S. Appl. No. 11/947,011.
U.S. Notice of Allowance dated Jan. 31, 2012, issued in corresponding U.S. Appl. No. 12/266,039.
U.S. Office Action dated Feb. 2, 2012, issued in corresponding U.S. Appl. No. 12/208,664.
U.S. Notice of Allowance dated Feb. 3, 2012, issued in corresponding U.S. Appl. No. 12/208,492.
U.S. Notice of Allowance dated Feb. 3, 2012, issued in corresponding U.S. Appl. No. 12/262,854.
U.S. Notice of Allowance dated Mar. 14, 2012, issued in corresponding U.S. Appl. No. 12/263,011.
U.S. Notice of Allowability dated Mar. 22, 2012, issued in corresponding U.S. Appl. No. 12/263,011.
U.S. Office Action dated Apr. 26, 2012, issued in corresponding U.S. Appl. No. 11/947,011.
U.S. Office Action dated May 10, 2012, issued in corresponding U.S. Appl. No. 12/247,338.
U.S Notice of Allowance dated Jul. 11, 2012, issued in corresponding U.S. Appl. No. 12/247,338.
Seong-Woo Choi et al., "*Synthesis, characterization and thermal degradation of functional benzoxazine monomers and polymers containing phenylphosphine oxide*", Polymer Degradation and Stability 91 (2006), pp. 1166-1178.
Seong-Woo Choi, et al., Polybenzoxazine Based Membrane with Enhanced Oxygen Permeability Inducing Fluorine Containing Benzoxazine Monomer as an Electrode Additive and Binder for High Temperature PEM Fuel Cells; slides of presentation at $212^{th}$ ECS, Washington, DC, Oct. 9, 2007.
STN Registry database entries for RN 35141-82-3, RN 35141-83-4 and RN 35141-84-5, Database entry date Nov. 16, 1984. Accessed Jan. 26, 2012.
Tarek AGAG, Journal of Applied Polymer Science, vol. 100, pp. 3769-3777 (2006).
$212^{th}$ ECS Meeting—Washington DC, Oct. 7-12, 2007, Program Information, B10—Proton Exchange Membrane Fuel Cells (PEMFC 7) Energy Technology/Physical and Analytical Electrochemistry/Battery/Industrial Electrochemistry and Electrochemical Engineering.
B. Antalek. "Using Pulsed Gradient Spin Echo NMR for Chemical Mixture Analysis: How to Obtain Optimum Results.", Concepts in Magnetic Resonance (2002) vol. 14(4), pp. 225-258.
S. Viel et al. "Diffusion-Ordered NMR Spectroscopy: A Versatile Tool for the Molecular Weight Determination of Uncharged Polysaccharides.", Biomacromolecules (2003) vol. 4, pp. 1843-1847.

D. A. Jayawickrama et al. "Polymer additives mixture analysis using pulsed-field gradient NMR spectroscopy.", Magn.Reson. Chem (1998), vol. 36, pp. 755-760.
K. Nishinari et al. "Soulution Properties of Pullulan.", Macromolecules (1991) vol. 24, pp. 5590-5593.
L.C. Van Gorkom et al. "Analysis of DOSY and GPC-NMR Experiments on Polymers by Multivariate Curve Resolution.", Journal of Magnetic Resonance (1998) vol. 130, pp. 125-130.
A. Chen et al. "Determination of Molecular Weight Distributions for Polymers by Diffusion-Ordered NMR.", J. Am. Chem. Soc. (1995) vol. 117, pp. 7965-7970.
Hajime Kimura et al. "Epoxy Resin Cured by Bisphenol a Based Benzoxazine.", Journal of Applied Polymer Science (1998), vol. 68, pp. 1903-1910.
Schuster, Martin F.H., et al., "Anhydrous Proton-Conducting Polymers", Annu. Rev. Mater. Res., vol. 33, 2003, pp. 233-261.
Yamada, M. et al., "Anhydrous proton conducting polymer electrolytes based on poly(vinylphosphonic acid)-heterocyclic composite material", Polymer, vol. 46, No. 9, 2005, pp. 2986-2992.
Pu, H., et al., "Proton Transport in Polybenzimidazole Blended with $H_3PO_4$ or $H_2SO_4$", J. Polymer Science, Part B: Polymer Physics, vol. 40, 2002, pp. 663-669.
Kim, Hyoung-Juhn et al. *Polybenzimidazoles for High Temperature Fuel Cell Application.* Macromol. Rapid Commun. 2004, vol. 25, pp. 1410-1413.
Ueda, Mitsuru et al. *Poly(benzimidazole) Synthesis by Direct Reaction of Methoxyphthalic Acids and Tetramine.* J. Poly. Sci. Part A: Polym. Chem, 27 pp. 2815-2818 (1989).
Choi et al., "Synthesis, characterization and thermal degradation of functional benzoxazine monomers and polymers containing phenylphosphine oxide", Polymer Degradation and Stability, vol. 91, No. 5, May 1, 2006, pp. 1166-1178.
Low, Hong Yee, et al. "Structural Effects of Phenols on the Thermal and Thermo-oxidative Degradation of Polybenzoxazines". Polymer, vol. 40, No. 15. Jul. 1999. pp. 4365-4376.
Kim, H.J., et al. "Synthesis and Thermal Characterization of Polybenzoxazines Based on Acetylene-functional Monomers". Polymer, vol. 40, No. 23. Nov. 1999. pp. 6565-6573.
Shen, Shyan Bob, et al. "Synthesis and Characterization of Polyfunctional Naphthoxazines and Related Polymers". Journal of Applied Polymer Science vol. 61, No. 9. 1996, pp. 1595-1605.
Lin et al., "Synthesis and Properties of Flame-Retardant Benzoxazines by Three Approaches", Journal of Polymer Science, Part A: Polymer Chemistry, vol. 44, 2006, pp. 3454-3468.
Hirai et al., "Air-Induced *anti*-Markovnikov Addition of Secondary Phosphine Oxides and H-Phosphinates to Alkenes", National Institute of Advanced Industrial Science and Technology, Organic Letters 2007, vol. 9, No. 1, pp. 53-55.
Beletskaya et al., "Arylation of 6*H*-Dibenzo[c,e][1,2 $\lambda^5$]oxaphosphinine 6-Oxide", Russian Journal of Organic Chemistry, vol. 40, No. 12, 2004, pp. 1782-1786.
Yamada et al., "A Novel Synthesis of 6-Hydroxyalkyl- and 6-Hydroxy-aralky1-6*H*-dibenz[c,e][1,2]oxaphosphorin 6-Oxides", vol. 27, 1990, pp. 845-850.
Human translation of JP 2003-286320, A. Takeichi et al., Oct. 2003.
Human translation of JP 2004-103494, Kimura et al., Apr. 2004.
Machine translation of JP 2004-149779, Sakaguchi et al., May 2004.
European Search Report issued in European Patent Application No. 06254551.2-2115 on Nov. 21, 2006.
European Office Action issued in corresponding European Patent Application No. 07250814.6 on Oct. 30, 2007.
European Search Report issued in European Patent Application No. 08104319.2 on Oct. 13, 2008.
European Search Report issued in European Patent Application No. 08157494.9 on Nov. 24, 2008.
European Office Action dated Dec. 4, 2008, issued in corresponding European Patent Application No. 08164095.5.
European Search Report issued in European Patent Application No. 08164096.3 on Jan. 20, 2009.
European Search Report issued in European Patent Application No. 08166328.8 on Jan. 22, 2009.
European Search Report issued in European Patent Application No. 08168081.1 on Jan. 28, 2009.
Extended European Search Report issued in European Patent Application No. 08168032.4 on Feb. 3, 2009.
European Search Report issued in European Patent Application No. 08168404.5 on Feb. 10, 2009.
Extended European Search Report issued in European Patent Application No. 08168404.5 on Apr. 23, 2009.
European Search Report dated Jul. 21, 2010 issued in corresponding European Patent Application No. 10164784.0.
European Search Report dated Jul. 21, 2010 issued in corresponding European Patent Application No. 10164785.7.
Japanese Office Action issued in Japanese Patent Application No. 2006-239572 on Feb. 17, 2009.
Japanese Office Action dated Jun. 21, 2011, issued in corresponding Japanese Patent Application No. 2007-309320.
Japanese Office Action dated Sep. 20, 2011, issued in corresponding Japanese Patent Application No. 2008-233675.
Japanese Office Action dated Oct. 23, 2011, issued in corresponding Japanese Patent Application No. 2007-309320.
Korean Office Action dated Jul. 21, 2010, issued in corresponding Korean Patent Application No. 10-2008-0089999.
Korean Office Action dated Oct. 6, 2010, issued in corresponding Korean Patent Application No. 10-2008-0099549.
U.S. Appl. No. 11/514,254, filed Sep. 1, 2006, Seong-woo Choi et al., Samsung SDI Co., Ltd.
U.S. Appl. No. 11/514,831, filed Sep. 5, 2006, Seong-woo Choi et al., Samsung SDI Co., Ltd.
U.S. Appl. No. 11/743,778, filed May 3, 2007, Seong-woo Choi et al., Samsung SDI Co., Ltd.
U.S. Appl. No. 11/856,350, filed Sep. 17, 2007, Seong-woo Choi et al., Samsung SDI Co., Ltd.
U.S. Appl. No. 11/947,011, filed Nov. 29, 2007, Seong-woo Choi et al., Samsung Electronics Co., Ltd.
U.S. Appl. No. 12/208,492, filed Sep. 11, 2008, Seong-woo Choi et al., Samsung Electronics Co., Ltd.
U.S. Appl. No. 12/208,664, filed Sep. 11, 2008, Seong-woo Choi et al., Samsung Electronics Co., Ltd.
U.S. Appl. No. 11/765,033, filed Jun. 19, 2007, Hee-young Sun et al., Samsung SDI Co., Ltd.
U.S. Appl. No. 12/247,338, filed Oct. 8, 2008, Seong-woo Choi et al., Samsung Electronics Co., Ltd.
U.S. Appl. No. 12/263,011, filed Oct. 31, 2008, Seong-woo Choi et al., Samsung Electronics Co., Ltd.
U.S. Appl. No. 12/262,854, filed Oct. 31, 2008, Seong-woo Choi et al., Samsung Electronics Co., Ltd.
U.S. Appl. No. 12/266,039, filed Nov. 6, 2008, Seong-woo Choi et al., Samsung Electronics Co., Ltd.
U.S. Appl. No. 13/464,517, filed May 4, 2012, Seong-woo Choi et al., Samsung Electronics Co., Ltd.
U.S. Appl. No. 13/466,750, filed May 8, 2012, Seong-woo Choi et al., Samsung Electronics Co., Ltd.
U.S. Appl. No. 13/478,893, filed May 23, 2012, Seong-woo Choi et al., Samsung Electronics Co., Ltd.
U.S. Appl. No. 13/523,516, filed Jun. 14, 2012, Seong-woo Choi et al., Samsung Electronics Co., Ltd.
U.S. Appl. No. 13/560,321, filed Jul. 27, 2012, Seong-woo Choi et al., Samsung Electronics Co., Ltd.

\* cited by examiner

*Primary Examiner* — Alicia L Otton
(74) *Attorney, Agent, or Firm* — Stein IP, LLC

(57) ABSTRACT

A naphthoxazine benzoxazine-based monomer is represented by Formula 1 below:

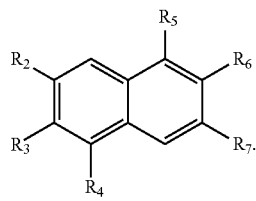

<Formula 1>

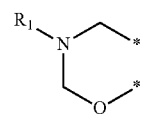

<Formula 2>

In Formula 1, $R_2$ and $R_3$ or $R_3$ and $R_4$ are linked to each other to form a group represented by Formula 2 below, and $R_5$ and $R_6$ or $R_6$ and $R_7$ are linked to each other to form a group represented by Formula 2 below, In Formula 2, * represents the bonding position of $R_2$ and $R_3$, $R_3$ and $R_4$, $R_5$ and $R_6$, or $R_6$ and $R_7$ of Formula 1. A polymer is formed by polymerizing the naphthoxazine benzoxazine-based monomer, an electrode for a fuel cell includes the polymer, an electrolyte membrane for a fuel cell includes the polymer, and a fuel cell uses the electrode.

11 Claims, 15 Drawing Sheets

NAPHTHOXAZINE BENZOXAZINE-BASED MONOMER, POLYMER THEREOF, ELECTRODE FOR FUEL CELL INCLUDING THE POLYMER, ELECTROLYTE MEMBRANE FOR FUEL CELL INCLUDING THE POLYMER, AND FUEL CELL USING THE ELECTRODE

CROSS-REFERENCE TO RELATED APPLICATIONS

This is a divisional application of U.S. application Ser. No. 12/262,854, filed Oct. 31, 2008, now issued as U.S. Pat. No. 8,188,280, which claims the benefit of Korean Patent Application No. 10-2007-111587, filed on Nov. 2, 2007, and Korean Patent Application. No. 10-2008-99351, filed on Oct. 9, 2008, in the Korean Intellectual Property Office, the disclosures of which are incorporated herein by reference.

BACKGROUND OF THE INVENTION

1. Field of the Invention

One or more embodiments of the present invention relate to a naphthoxazine benzoxazine-based monomer, a polymer thereof, an electrode for a fuel cell including the polymer, an electrolyte membrane for a fuel cell including the polymer, and a fuel cell using the electrode.

2. Description of the Related Art

Fuel cells, which use a polymer electrolyte membrane as an electrolyte, operate at a relatively low temperature and can be small in size. Thus, fuel cells may be used as power sources in electric vehicles or distributed generation systems for homes. As a polymer electrolyte membrane used in polymer electrolyte fuel cells, a perfluorocarbonsulfonic acid-based polymer membrane such as NAFION (registered trademark) has been used.

However, such polymer electrolyte membranes typically need water to provide proton conduction abilities, and thus the polymer electrolyte membranes typically need to be humidified. In addition, to enhance cell system efficiencies, it may be necessary to operate polymer electrolyte membranes at a high temperature of at least 100° C. However, the moisture in polymer electrolyte membranes may evaporate at this temperature, and the polymer electrolyte membranes may not function properly as a solid electrolyte.

To address those problems in the art, non-humidified electrolyte membranes that can operate at a high temperature of at least 100° C. under nonhumidified conditions have been developed. For example, U.S. Pat. No. 5,525,436 discloses polybenzimidazole doped with a phosphoric acid, and the like as a material constituting non-humidified electrolyte membranes.

In addition, in cells that operate at a low temperature, such as cells using a perfluorocarbonsulfonic acid-based polymer membrane, to prevent gas diffusion in electrodes due to water (formation water) that is produced as electricity is generated in an electrode, particularly a cathode, electrodes using polytetrafluoroethylene (PTFE) as a waterproof agent to have hydrophobic properties have been widely used (see, for example, Japanese Patent Laid-Open Publication No. hei 05-283082).

In addition, phosphoric acid type fuel cells operating at a high temperature of 150 to 200° C. use a liquid phosphoric acid as an electrolyte. However, a large amount of the liquid phosphoric acid is present in electrodes, which interferes with gas diffusion. Therefore, an electrode catalyst layer that is formed by adding polytetrafluoroethylene (PTFE) as a waterproof agent to an electrode catalyst, and which can prevent fine pores in electrodes from being clogged by a phosphoric acid, has been used.

In addition, in fuel cells using a polybenzimidazole (PBI) electrolyte membrane, which retains phosphoric acid as a nonhumidified electrolyte at a high temperature, to reduce contact between electrodes and the electrolyte membrane, a method of impregnating electrodes with a liquid phosphoric acid has been tried and a method of increasing a loading amount of metal catalysts has been tried. However, such fuel cells have not exhibited improved properties, and thus there is a need for improvement.

In addition, when air is supplied to a cathode when a solid polymer electrolyte doped with phosphoric acid is used, the fuel cell requires an aging time of about 1 week even if the composition of the cathode is optimized. By supplying oxygen to the cathode instead of air, performance of the cathode can be improved and aging time can also be reduced. However, the need to supply of oxygen to the cathode is an obstacle in realizing widespread use of the cathode.

SUMMARY OF THE INVENTION

One or more embodiments of the present invention include a naphthoxazine benzoxazine-based monomer, a polymer thereof, an electrode for a fuel cell including the polymer, an electrolyte membrane for a fuel cell including the polymer, and a fuel cell which includes an electrode for a fuel cell formed using the polymer thereof, thereby having improved cell performance.

Additional aspects and/or advantages will be set forth in part in the description which follows and, in part, will be apparent from the description, or may be learned by practice of the invention.

According to an embodiment of the present invention, there is provided a naphthoxazine benzoxazine-based monomer represented by Formula 1 below:

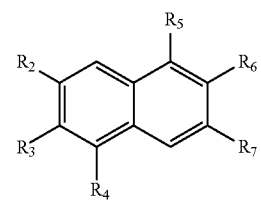
<Formula 1> wherein $R_2$ and $R_3$ or $R_3$ and $R_4$ are linked to each other to form a group represented by Formula 2 below, and $R_5$ and $R_6$ or $R_6$ and $R_7$ are linked to each other to form a group represented by Formula 2 below,

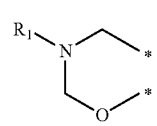
<Formula 2>

Wherein, in Formula 2, $R_1$ is a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ carbocycle group, a substituted or unsubstituted $C_4$-$C_{20}$ carbocyclic alkyl group, a substituted or unsubstituted $C_2$-$C_{20}$ heterocycle group, or a substituted or unsubstituted $C_2$-$C_{20}$ heterocyclic alkyl group, in Formula 2, * represents the bonding position of $R_2$ and $R_3$, $R_3$ and $R_4$, $R_5$ and $R_6$, or $R_6$ and $R_7$ of Formula 1, and $R_2$ or $R_4$ that does not form a group of Formula 2 is hydrogen and $R_5$ or $R_7$ that does not form a group of Formula 2 is hydrogen.

According to an embodiment of the present invention, there is provided a polymer of a naphthoxazine benzoxazine-based monomer which is a polymerization product of the naphthoxazine benzoxazine-based monomer described above or a polymerization product of the naphthoxazine benzoxazine-based monomer described above and a crosslinkable compound.

According to an embodiment of the present invention, there is provided an electrode for a fuel cell, the electrode comprising a catalyst layer comprising the polymer of the naphthoxazine benzoxazine-based monomer.

According to an embodiment of the present invention, there is provided an electrolyte membrane for a fuel cell, the electrolyte membrane comprising the polymer of the naphthoxazine benzoxazine-based monomer.

According to an embodiment of the present invention, there is provided a fuel cell comprising a cathode; an anode; and an electrolyte membrane interposed between the cathode and the anode, wherein at least one of the cathode and the anode comprises a catalyst layer comprising the polymer of the naphthoxazine benzoxazine-based monomer described above or wherein the electrolyte membrane comprises the polymer of the naphthoxazine benzoxazine-based monomer described above.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF THE EMBODIMENTS

Figure 1:
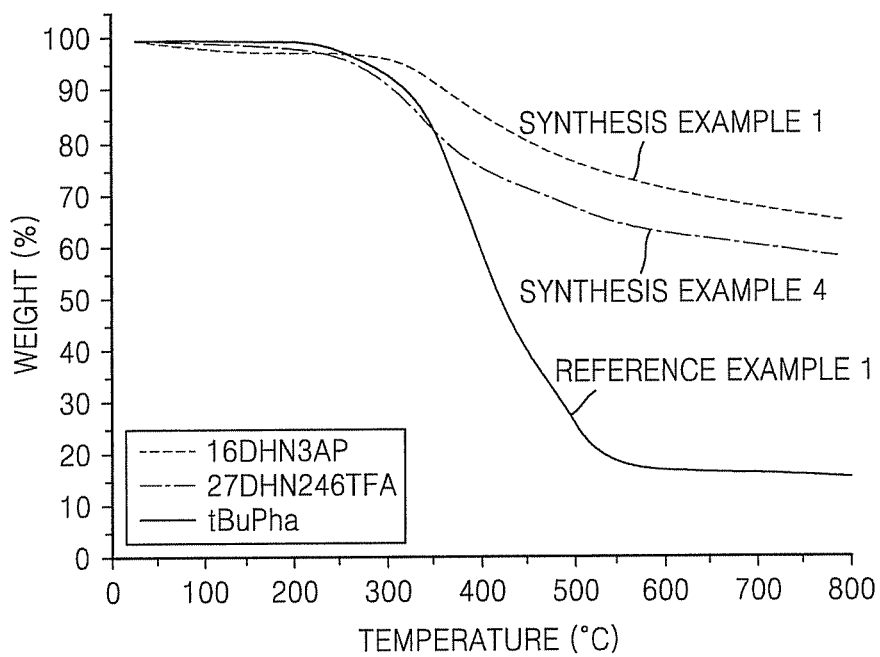
FIG. 1 is a graph showing thermogravimetric analysis (TGA) results of a compound prepared in Synthesis Example 1, a compound prepared in Synthesis Example 4, and t-BuPh-a prepared in Reference Example 1.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

A naphthoxazine benzoxazine-based monomer according to an embodiment of the present invention is represented by Formula 1 below:

<Formula 1>

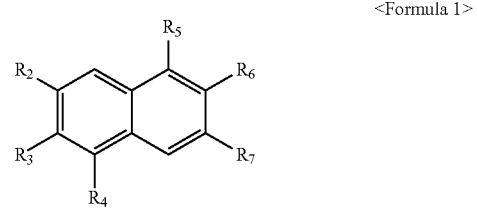

wherein $R_2$ and $R_3$ or $R_3$ and $R_4$ are linked to each other to form a group represented by Formula 2 below, and $R_5$ and $R_6$ or $R_6$ and $R_7$ are linked to each other to form a group represented by Formula 2 below.

<Formula 2>

In Formula 2, $R_1$ is a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a substituted or unsubstituted $C_6$-$C_{20}$ aryl group, a substituted or unsubstituted $C_6$-$C_{20}$ aryloxy group, a substituted or unsubstituted $C_7$-$C_{20}$ arylalkyl group, a substituted or unsubstituted $C_2$-$C_{20}$ heteroaryl group, a substituted or unsubstituted $C_2$-$C_{20}$ heteroaryloxy group, a substituted or unsubstituted $C_2$-$C_{20}$ heteroarylalkyl group, a substituted or unsubstituted $C_4$-$C_{20}$ carbocyclic group, a substituted or unsubstituted $C_4$-$C_{20}$ carbocyclic alkyl group, a substituted or unsubstituted $C_2$-$C_{20}$ heterocyclic group, or a substituted or unsubstituted $C_2$-$C_{20}$ heterocyclic alkyl group, In Formula 2, * represents the bonding position of $R_2$ and $R_3$, $R_3$ and $R_4$, $R_5$ and $R_6$, or $R_6$ and $R_7$, respectively, of Formula 1, and $R_2$ or $R_4$ that does not form a group of Formula 2 is hydrogen and $R_5$ or $R_7$ that does not form a group of Formula 2 is hydrogen.

As non-limiting examples, $R_1$ may be one selected from groups represented by the following formulae.

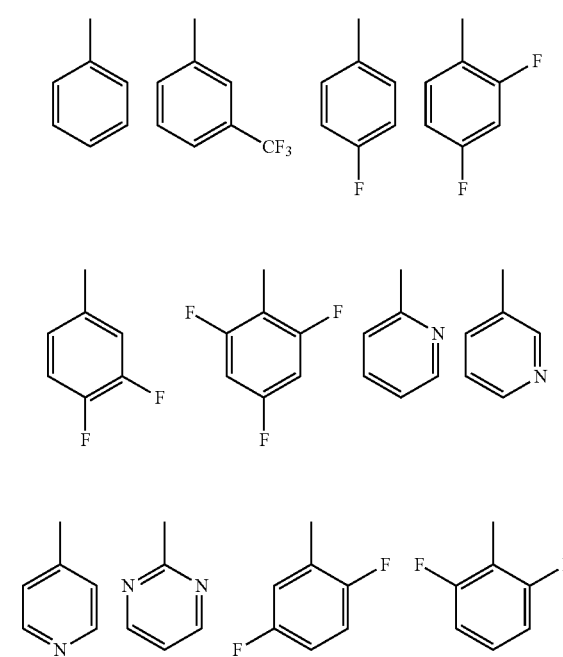

As non-limiting examples, the naphthoxazine benzoxazine-based monomer may be at least one selected from compounds represented by Formulae 3 through 5.

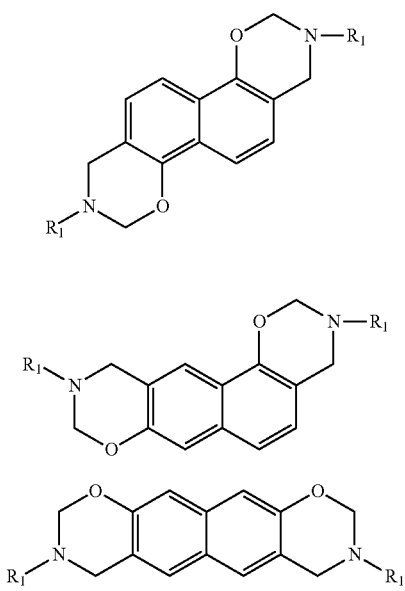

In Formulae 3 through 5, $R_1$ may be a group as defined in Formula 1, and, as non-limiting examples, may be selected from groups represented by the following formulae.

The naphthoxazine benzoxazine-based monomer according to aspects of the present invention has structural stiffness due to an increase in crosslinked sites. In addition, when the naphthoxazine benzoxazine-based monomer is used in forming an electrode for a fuel cell, fluorine, a fluorine-containing functional group, or a pyridine functional group is introduced into the monomer as described above, and thus oxygen transmittance and an amount of phosphoric acid injected into the electrode can be increased and thermal resistance and resistance to phosphoric acid can be obtained at the same time.

In addition, the naphthoxazine benzoxazine-based monomer according to an embodiment of the present invention includes a naphthoxazine group that can maximize a hydrogen bond in a molecule and a hydrogen bond between molecules, and thus, when the naphthoxazine benzoxazine-based monomer is co-polymerized with a crosslinkable compound, the number of crosslinkable sites increases. Thus, by using the naphthoxazine benzoxazine-based monomer, a fuel cell that can have excellent thermal stability and durability at an operating temperature, and thereby having a long lifetime, can be prepared.

In addition, when the naphthoxazine benzoxazine-based monomer is simultaneously used in an electrode and an electrolyte membrane, the compatibility of an interface between the electrolyte membrane and the electrode is enhanced. Thus, the performance of a fuel cell can be maximized.

The naphthoxazine benzoxazine-based monomer represented by Formula 1 may be one selected from compounds represented by Formulae 6 through 11.

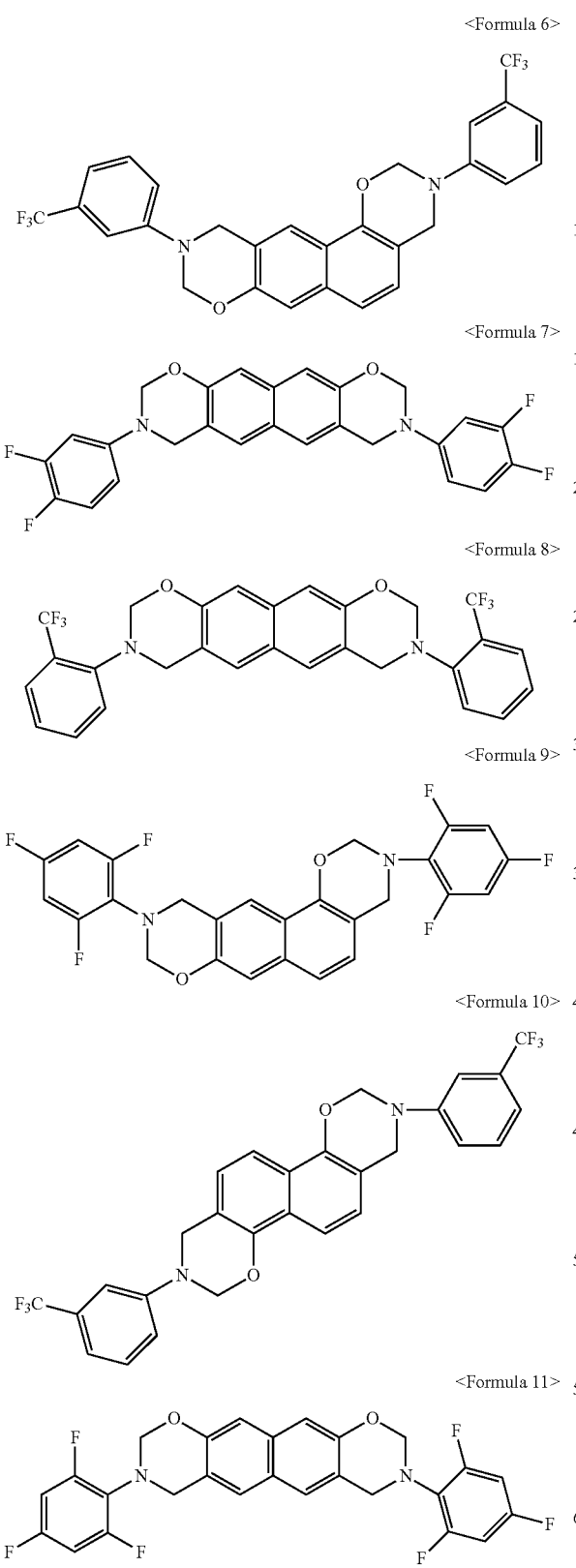

<Formula 6>
<Formula 7>
<Formula 8>
<Formula 9>
<Formula 10>
<Formula 11>

Hereinafter, a method of preparing the naphthoxazine benzoxazine-based monomer of Formula 1 according to aspects of the present invention will be described. As an embodiment of the present invention, a method of preparing the compounds represented by Formulae 3 through 5 will now be described; however, the other compounds described above can be synthesized in a manner similar to the preparation method described herein.

Referring to Reaction Scheme 1 below, the compound of Formula 3 can be prepared by heating 1,5-dihydroxynaphthalene (A), p-formaldehyde (B) and an amine compound (C) without a solvent or by adding a solvent to A, B and C and then refluxing the mixture, and thereafter working up the resultant. Referring to Reaction Schemes 2 and 3, the compound of Formula 4 and the compound of Formula 5 can be prepared in the same manner as in Reaction Scheme 1, except that 1,6-dihydroxynaphthalene (A') or 2,7-dihydroxynaphthalene (A") are used instead of 1,5-dihydroxynaphthalene (A).

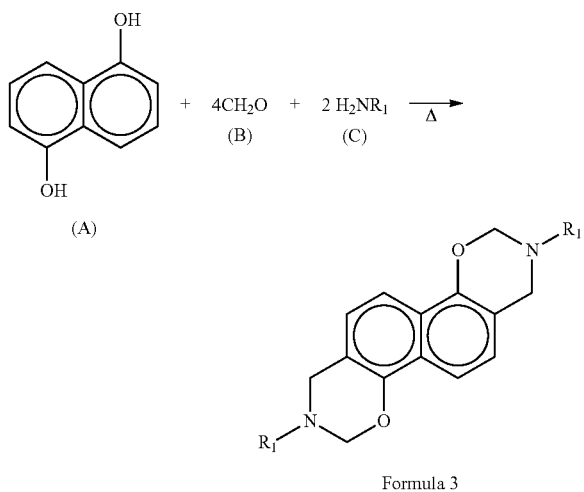

<Reaction Scheme 1>

Formula 3

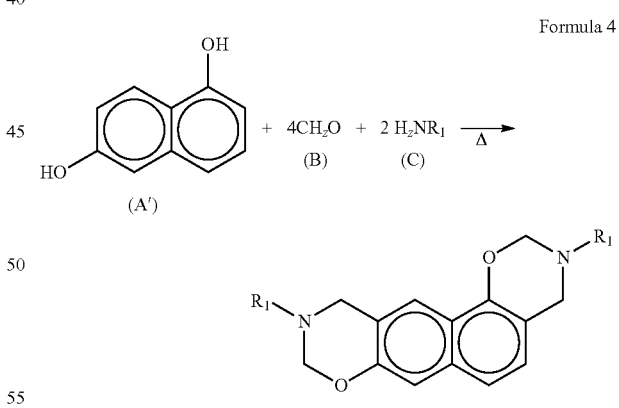

<Reaction Scheme 2>

Formula 4

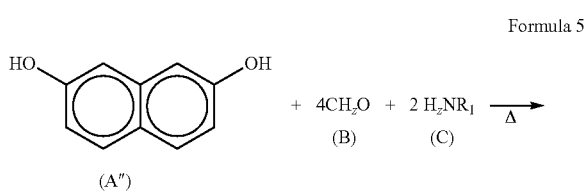

<Reaction Scheme 3>

Formula 5

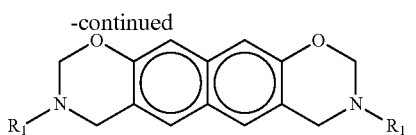

In Reaction Schemes 1 through 3, $R_1$ may be selected from the same groups represented by the following formulae as defined in Formulae 3 through 5.

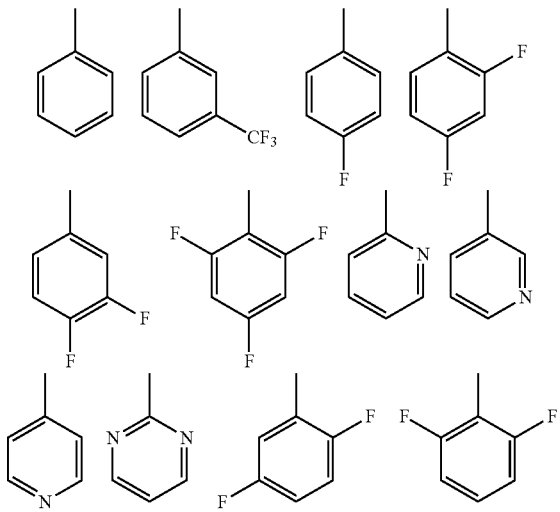

The solvent used in the reactions described above may be 1,4-dioxane, chloroform, dichloromethane, THF, or the like. The heating temperature is adjusted to a temperature range that can reflux the solvent, such as, for example, a range of 80 to 110° C., or more specifically, about 110° C.

As a non-limited embodiment of the working-up process, the resultant reaction mixture is washed with an aqueous 1N NaOH solution and water and dried using a drier such as magnesium sulfate, and then the resultant is filtered and evaporated under reduced pressure in order to remove the solvent from the resultant, and dried to obtain a target material.

Non-limiting examples of the $C_1$-$C_{20}$ alkyl group" include methyl, ethyl, propyl, isobutyl, sec-butyl, pentyl, iso-amyl, hexyl, or the like. The $C_1$-$C_{20}$ alkyl group may be unsubstituted, or at least one hydrogen atom of the alkyl group may be substituted with a halogen atom such as fluorine and chlorine, a $C_1$-$C_{20}$ alkyl group substituted with a halogen atom (such as, for example, $CCF_3$, $CHCF_2$, $CH_2F$, $CCl_3$, and the like), a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_5$-$C_{20}$ heteroaryl group, a $C_1$-$C_{20}$ heterocyclic group, or a $C_6$-$C_{20}$ heteroarylalkyl group.

The term "aryl group" as used herein refers to a $C_6$-$C_{20}$ carbocyclic aromatic system containing at least one ring, wherein the rings can be pendantly attached to each other or fused with each other. The term "aryl," as used alone or in combination with other terms, refers to an aromatic radical, such as, for example, phenyl, naphthyl, tetrahydronaphthyl, such as, or the like. The aryl group may be unsubstituted or at least one hydrogen atom of the aryl group may be substituted with a substituent described above with respect to the alkyl group.

As non-limiting examples, the aryloxy group may be a phenoxy group, a naphthyloxy group, a tetrahydronaphthyloxy group, or the like. The aryloxy group may be unsubstituted or at least one hydrogen atom of the aryloxy group may be substituted with a substituent described above with respect to the alkyl group.

The term "heteroaryl group" as used herein refers to a monovalent, monocyclic or bicyclic aromatic bivalent organic compound that contains 1, 2 or 3 hetero atoms selected from the group consisting of N, O, P, and S and has 1 to 20 carbon atoms. As non-limiting examples, the heteroaryl group may be pyrazinyl, furanyl, thienyl, pyridyl, pyrimidinyl, isothiazolyl, oxazolyl, thiazolyl, triazolyl, 1,2,4-thiadiazolyl, or the like. The heteroaryl group may be unsubstituted or at least one hydrogen atom of the heteroaryl group may be substituted with a substituent described above with respect to the alkyl group.

As non-limiting examples, the heteroaryloxy group may be pyrazinyloxy, furanyloxy, thienyloxy, pyridyloxy, pyrimidinyloxy, isothiazolyloxy, oxazolyloxy, thiazolyloxy, triazolyloxy, 1,2,4-thiadiazolyloxy, or the like. The heteroaryloxy group may be unsubstituted or at least one hydrogen atom of the heteroaryloxy group may be substituted with the a substituent described above with respect to the alkyl group.

The term "heterocyclic group" as used herein refers to a 5 to 10 membered group containing a hetero atom such as nitrogen, sulfur, phosphorus, oxygen, and the like. The heterocyclic group may be unsubstituted or at least one hydrogen atom of the heterocycle group may be substituted with a substituent described above with respect to the alkyl group.

As non-limiting examples, the cycloalkyl group may be a cyclohexyl group, a cyclopentyl group, or the like. The cycloalkyl group may be unsubstituted or at least one hydrogen atom of the cycloalkyl group may be substituted with a substituent described above with respect to the alkyl group.

An embodiment of the present invention also provides a polymer of the naphthoxazine benzoxazine-based monomer of Formula 1.

The polymer can be prepared by dissolving the naphthoxazine benzoxazine-based monomer of Formula 1 in a solvent, and then polymerizing the resultant by a heat treatment, such as, for example, a heat treatment at a temperature range of 180 to 250° C. When the heat treatment temperature is less than 180° C., reactivity of polymerization may be degraded. On the other hand, when the heat treatment temperature is greater than 250° C., an unreacted compound may be produced so that the product yield may be reduced.

In this reaction, a polymerization catalyst, and the like can be used, if necessary.

The solvent used in the polymerization reaction may be N-methylpyrrolidone (NMP), dimethylacetamide (DMAc), or the like, and the amount of the solvent may be in the range of 5 to 30 parts by weight based on 100 parts by weight of the naphthoxazine benzoxazine-based monomer of Formula 1.

An embodiment of the present invention also provides a polymer that is a polymerization product of the naphthoxazine benzoxazine-based monomer of Formula 1 and a crosslinkable compound.

The crosslinkable compound may be at least one of polybenzimidazole, a polybenzimidazole-base complex, polybenzthiazole, polybenzoxazole and polyimide.

The amount of the crosslinkable compound may be in the range of 5 to 95 parts by weight based on 100 parts by weight of the naphthoxazine benzoxazine-based monomer of Formula 1.

When the polymer of the naphthoxazine benzoxazine-based monomer of Formula 1 according to aspects of the present invention is used in forming an electrode for a fuel cell, oxygen transmission is improved even when only air is supplied to a cathode, and wettability of phosphoric acid ($H_3PO_4$) in an electrode and thermal stability can be improved.

In addition, when the polymer of the naphthoxazine benzoxazine-based monomer is used in forming an electrolyte membrane for a fuel cell, thermal stability and durability of the electrolyte membrane at an operating temperature are improved.

Therefore, a fuel cell employing the electrode and an electrolyte membrane can operate at a high temperature under nonhumidified conditions, can have enhanced thermal stability, and can exhibit improved electricity generation performance.

The electrode for a fuel cell, according to aspects of the present invention includes a catalyst layer comprising a polymerization product of the naphthoxazine benzoxazine-based monomer of Formula 1 or a polymer of the naphthoxazine benzoxazine-based monomer of Formula 1 and a crosslinkable compound. The catalyst layer includes a catalyst. The polymer of the naphthoxazine benzoxazine-based monomer represented by Formula 1 may be used as a binder of the electrode, and in particular, can act as a binder. Thus, a commonly used binder is not necessary for the electrode.

The polymer of the naphthoxazine benzoxazine-based monomer of Formula 1 is a material that improves wettability of phosphoric acid. The amount of the polymer may be in the range of 0.1 to 65 parts by weight based on 100 parts by weight of the catalyst. When the amount of the polymer of the naphthoxazine benzoxazine-based monomer of Formula 1 is less than 0.1 parts by weight based on 100 parts by weight of the catalyst, wettability of phosphoric acid in an electrode may be insufficiently improved. On the other hand, when the amount of the polymer of the naphthoxazine benzoxazine-based monomer of Formula 1 is greater than 65 parts by weight based on 100 parts by weight of the catalyst, membrane forming properties may be decreased.

The catalyst may be platinum alone, or an alloy or mixture of platinum and at least one metal selected from the group consisting of gold, palladium, rhodium, iridium, ruthenium, tin, molybdenum, cobalt, and chrome. Alternatively, the catalyst may be a support catalyst in which the catalyst metal is loaded on a carbonaceous support. In particular, the catalyst may be a catalyst metal including at least one of Pt, PtCo, and PtRu, or a support catalyst in which the catalyst metal is loaded on a carbonaceous support.

The electrode may further include a binder that can be conventionally used in the preparation of an electrode for a fuel cell.

As non-limiting examples, the binder may be at least one selected from the group consisting of poly(vinylidenefluoride), polytetrafluoroethylene, tetrafluoroethylene-hexafluoropropylene copolymer, and perfluoroethylene. The amount of the binder may be in the range of 0.1 to 50 parts by weight based on 100 parts by weight of the catalyst. When the amount of the binder is less than 0.1 parts by weight based on 100 parts by weight of the catalyst, the adhesion between electrodes may be so poor that it may be difficult to maintain the shape of a catalyst layer. On the other hand, when the amount of the binder is greater than 50 parts by weight based on 100 parts by weight of the catalyst, an electric resistance in the electrode may be increased.

The type and amount of the crosslinkable compound may be the same as described above.

A method of preparing the electrode for a fuel cell described above is as follows.

First, a catalyst is dispersed in a solvent to obtain a dispersion. The solvent used may be N-methylpyrrolidone (NMP), dimethylformamide (DMAc), or the like, and the amount of the solvent may be in the range of 100 to 1,000 parts by weight based on 100 parts by weight of the catalyst.

A mixture of the naphthoxazine benzoxazine-based monomer of Formula 1 and a solvent is added to the dispersion and mixed together, and then the resultant is stirred. The mixture may further include a binder and a crosslinkable compound. The solvent may be N-methylpyrrolidone (NMP), dimethylacetamide (DMAc), or the like.

The resultant is coated on the surface of a carbon support to prepare an electrode. The carbon support may be fixed on a glass substrate in order to easily coat the resultant thereon. The coating method is not particularly limited, but, may be coating using a doctor blade, bar coating, screen printing, or the like.

The coated resultant is dried at a temperature in the range of 20 to 150° C., to remove the solvent. The drying time is dependent on the drying temperature, and may be in the range of 10 to 60 minutes.

As can be seen in the method of preparing an electrode described above, the electrode for a fuel cell contains a polymer of the naphthoxazine benzoxazine-based monomer of Formula 1. The naphthoxazine benzoxazine-based monomer of Formula 1 is polymerized during the drying process described above and/or while a fuel cell including the electrode operates.

If a crosslinking agent is further added to the mixture of the naphthoxazine benzoxazine-based monomer, the solvent, and the binder, the prepared electrode includes a polymer of the benzoxazine-based monomer and the crosslinking agent.

Hereinafter, an electrolyte membrane and a method of preparing the electrolyte membrane according to an embodiment of the present invention will be described. An electrolyte membrane formed using a crosslinkable compound is described herein. However, when an electrolyte membrane is prepared only using the naphthoxazine benzoxazine-based monomer of Formula 1, the preparation process is the same as that described herein, except that the crosslinkable compound is not used.

As a first method, the naphthoxazine benzoxazine-based monomer represented by Formula 1 may be blended with a crosslinkable compound, and the mixture is cured at a temperature in the range of 50 to 250° C., or more specifically, 80 to 220° C. The cured mixture is impregnated with a proton conductor such as an acid to prepare an electrolyte membrane.

The cross-linkable compound may be at least one selected from polybenzimidazoles (PBI), polybenzimidazole-base complexes, polybenzthiazoles, polybenzoxazoles, and polyimides. For example, polybenzimidazole-base complexes are disclosed in Korean Patent No. 2007-102579.

The amount of the crosslinkable compound may be in the range of 5 to 95 parts by weight based on 100 parts by weight of the naphthoxazine benzoxazine-based monomer of Formula 1. When the amount of the crosslinkable compound is less than 5 parts by weight, phosphoric acid may not be sufficiently impregnated. On the other hand, when the amount of the crosslinkable compound is greater than 95 parts by weight, the crosslinked object may be partially dissolved in a polyphosphoric acid in the presence of an excessive amount of phosphoric acid.

As a second method, an electrolyte membrane may be formed using a mixture of the naphthoxazine benzoxazine-based monomer represented by Formula 1 and a crosslinkable compound.

The formation of the electrolyte membrane may be performed by a tape casting method, or a conventional coating method. The conventional coating method may be a method in which the mixture is cast onto a support using a doctor blade. Herein, a doctor blade with a 250 to 500 μm gap may be used.

When the casting method using a doctor blade is used, the process of forming the electrolyte membrane further includes separating the electrolyte membrane from the support, between the time when curing of the mixture occurs and the time when impregnation of the resultant with acid occurs. To separate the electrolyte membrane from the support, the mixture is immersed in distilled water at temperature range of 60 to 80° C.

The support can be any support that can support an electrolyte membrane, such as, for example, a glass substrate, a polyimide film, and the like. When the tape casting method is used, a tape cast membrane is separated from a support such as polyethyleneterephthalate before being cured, and then put into an oven.

In addition, when a membrane is formed by the tape casting method using a mixture of a benzoxazine-based monomer and polybenzimidazole, a process of filtering the mixture may be further performed.

The tape cast membrane is cured by heat treatment, and then is impregnated with a proton conductor such as acid to form an electrolyte membrane.

Non-restrictive examples of the proton conductor include a phosphoric acid, and a $C_1$-$C_{20}$ organic phosphonic acid. As non-limiting examples, the $C_1$-$C_{20}$ organic phosphonic acid may be methyl phosphonic acid or ethyl phosphonic acid.

The amount of the proton conductor may be in the range of 300 to 1,000 parts by weight based on 100 parts by weight of the total weight of the electrolyte membrane. The concentration of the acid used is not particularly limited. As a non-limiting example, if phosphoric acid is used as the proton conductor, a 85 wt % aqueous phosphoric acid solution may be used, and the impregnation time of the phosphoric acid may be in the range of 2.5 to 14 hours at 80° C.

A method of preparing a fuel cell using the electrode for a fuel cell according to an embodiment of the present invention will now be described.

Any electrolyte membrane that is commonly used in the preparation of fuel cells can be used herein. For example, the electrolyte membrane that is commonly used in a fuel cell may be a polybenzimidazole electrolyte membrane, a polybenzoxazine-polybenzimidazole copolymer electrolyte membrane, a PTFE porous membrane, or the like.

Alternatively, an electrolyte membrane including a crosslinked product prepared by polymerization of the naphthoxazine benzoxazine-based monomer represented by Formula 1 and a crosslinkable compound may be used.

In particular, performance of the fuel cell including the electrode as described herein may be maximized by using the electrolyte membrane including the polymer that is a crosslinked product prepared by polymerization of the naphthoxazine benzoxazine-based monomer represented by Formula 1 and a crosslinkable compound.

A method of preparing a membrane-electrode assembly for a fuel cell, according to aspects of the present invention, is as follows. The term "membrane and electrode assembly (MEA)" used herein refers to a structure in which electrodes, each comprising a catalyst layer and a diffusion layer, are deposited on respective surfaces of the electrolyte membrane.

The MEA may be formed by positioning the electrodes each including the catalyst layer for an electrode described above at respective sides of the electrolyte membrane, joining the electrolyte membrane and electrodes together at a high temperature and a high pressure, and then joining a fuel diffusion layer to the catalyst layers.

Herein, the joining is performed under a pressure in the range of 0.1 to 3 ton/cm$^2$, or more specifically, at a pressure of about 1 ton/cm$^2$, in a state reached when the MEA is heated up to a temperature that softens the electrolyte membrane.

Next, a bipolar plate is disposed on each side of the membrane-electrode assembly to prepare a fuel cell. The bipolar plate has grooves used for supplying fuel, and functions as a current collector.

The use of the fuel cell according to aspects of the present invention is not particularly limited. For example, the fuel cell may be used as a polymer electrolyte membrane (PEM) fuel cell.

Hereinafter, aspects of the present invention will be described more specifically with reference to the following examples. The following examples are only for illustrative purposes and are not intended to limit the scope of the invention.

Synthesis Example 1

Preparation of 16DHN-3AP represented by Formula 6

3.0 g of 1,6-dihydroxynaphthalene (18.7 mmol), 2.6 g of para-formaldehyde (82.4 mmol), and 3.88 g of 3-aminopyridine (41.2 mmol) were sequentially added to a 100 ml one-neck round bottomed flask, and then mixed in an oil bath at 90° C.

The reaction mixture was transparent in an early stage of the reaction, and about 30 minutes after the reaction, the reaction mixture was converted into a dark brown material in the form of a transparent gel. The reaction mixture was quenched with tetrahydrofurane (THF) to be cooled to room temperature. The crude product cooled to room temperature was base washed twice by solvent extraction using an aqueous 1N NaOH solution, and then washed once again with deionized water.

After the washing process was terminated, an organic layer was dried using MgSO$_4$, and then continuously filtered. The filtered solution was removed using a rotary evaporator, and then the purified product was dried in a vacuum oven at 40° C. for 6 hours to obtain the target material.

Figure 4:
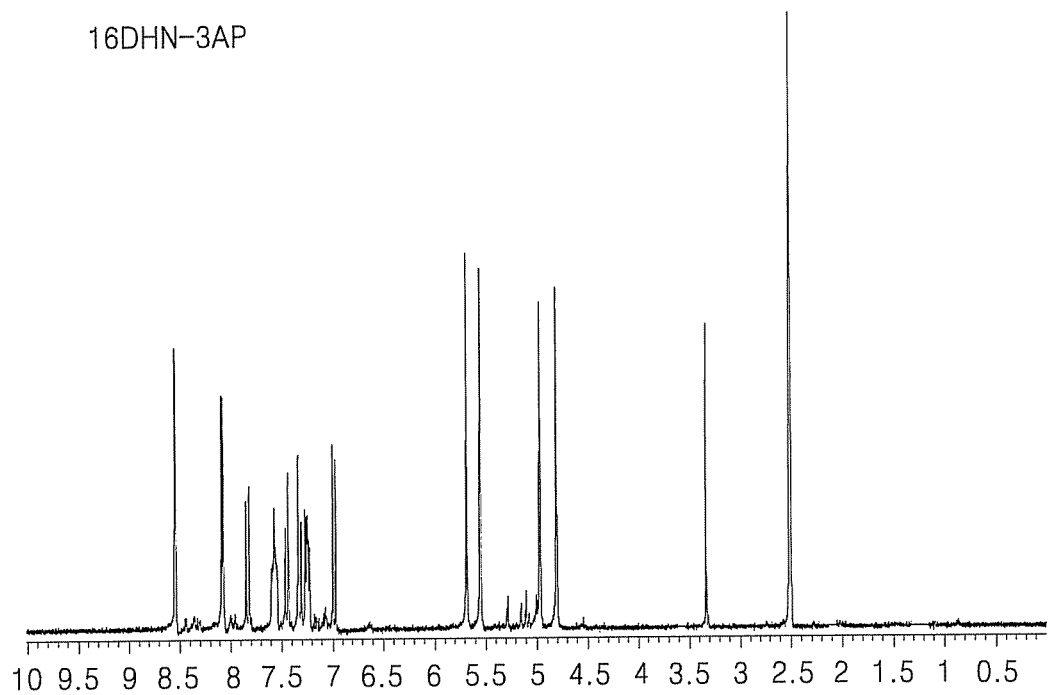
FIGS. 4 through 9 are graphs showing nuclear magnetic resonance (NMR) spectra of target materials prepared in Synthesis Examples 1 through 5, respectively.

FIG. 4 shows the nuclear magnetic resonance (NMR) spectrum of the target material prepared in Synthesis Example 1. The structure of the target material was confirmed by its NMR spectrum as shown in FIG. 4.

Synthesis Example 2

Preparation of 27DHN-34DFA Represented by Formula 7

A target material was prepared in the same manner as in Synthesis Example 1, except that 14.41 g of 2,7-dihydroxynaphthalene (0.09 mmol), 12.33 g of para-formaldehyde (0.39 mmol), and 25 g of 3,4-difluoroaniline (0.194 mmol) were added to a 100 ml one-neck round bottom flask instead of the materials described in Synthesis Example 1.

Figure 5:
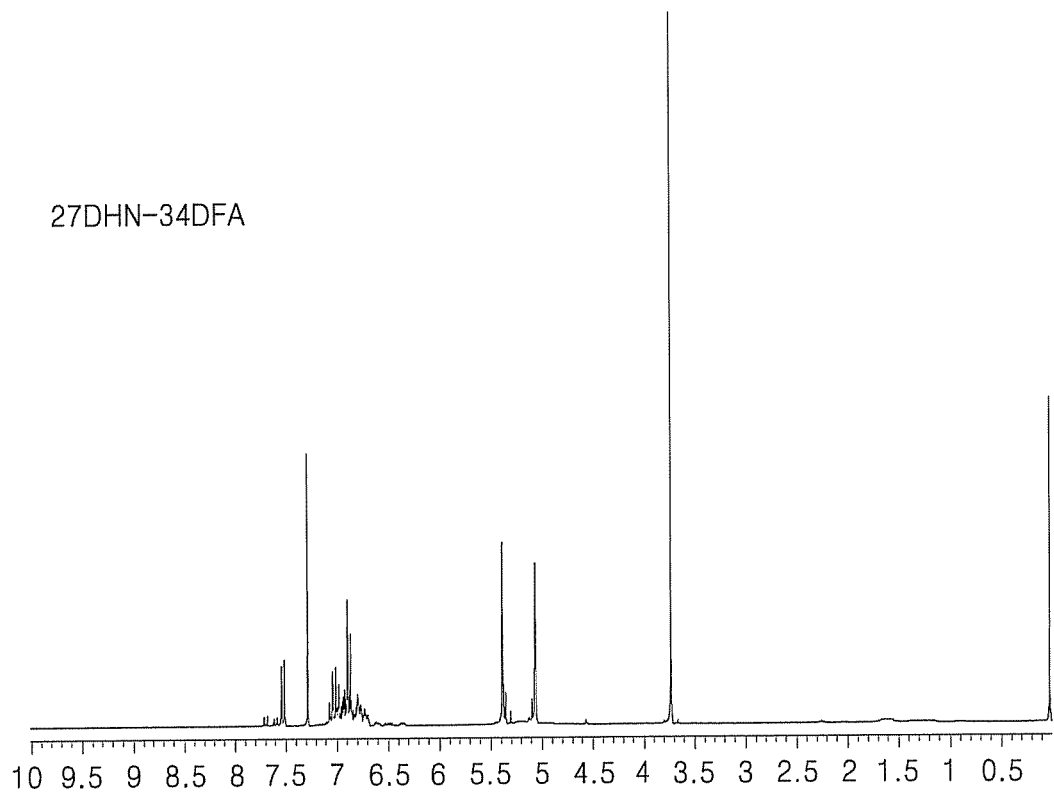

FIG. 5 shows the NMR spectrum of the target material prepared in Synthesis Example 2. The structure of the target material was confirmed by its NMR spectrum as shown in FIG. 5.

Synthesis Example 3

Preparation of 27DHN-2AP Represented by Formula 8

A target material was prepared in the same manner as in Synthesis Example 1, except that 3.0 g of 2,7-dihydroxynaphthalene (18.7 mmol), 2.6 g of para-formaldehyde (82.4 mmol), and 3.88 g of 2-aminopyridine (41.2 mmol) were added to a 100 ml one-neck round bottom flask instead of the materials described in Synthesis Example 1.

Figure 6:
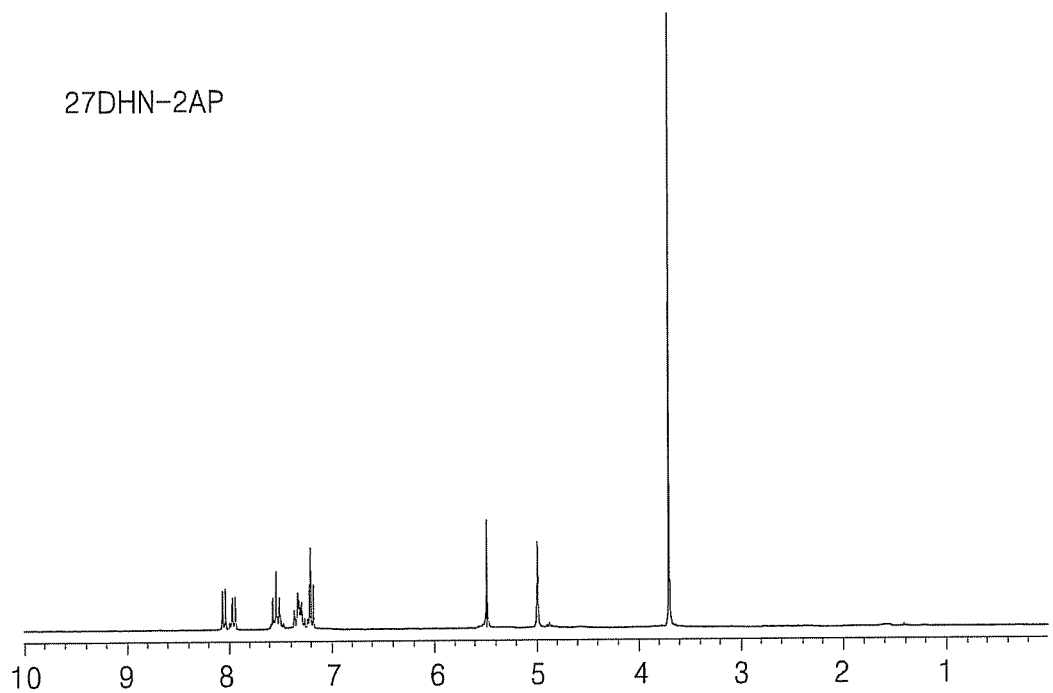

FIG. 6 shows the NMR spectrum of the target material prepared in Synthesis Example 3. The structure of the target material was confirmed by its NMR spectrum as shown in FIG. 6.

Synthesis Example 4

Preparation of 16DHN246TFA Represented by Formula 9

A target material was prepared in the same manner as in Synthesis Example 1, except that 6.06 g of 2,4,6-trifluoroaniline (41.2 mmol) was used instead of 3.88 g of 3-aminopyridine (41.2 mmol).

Figure 7:
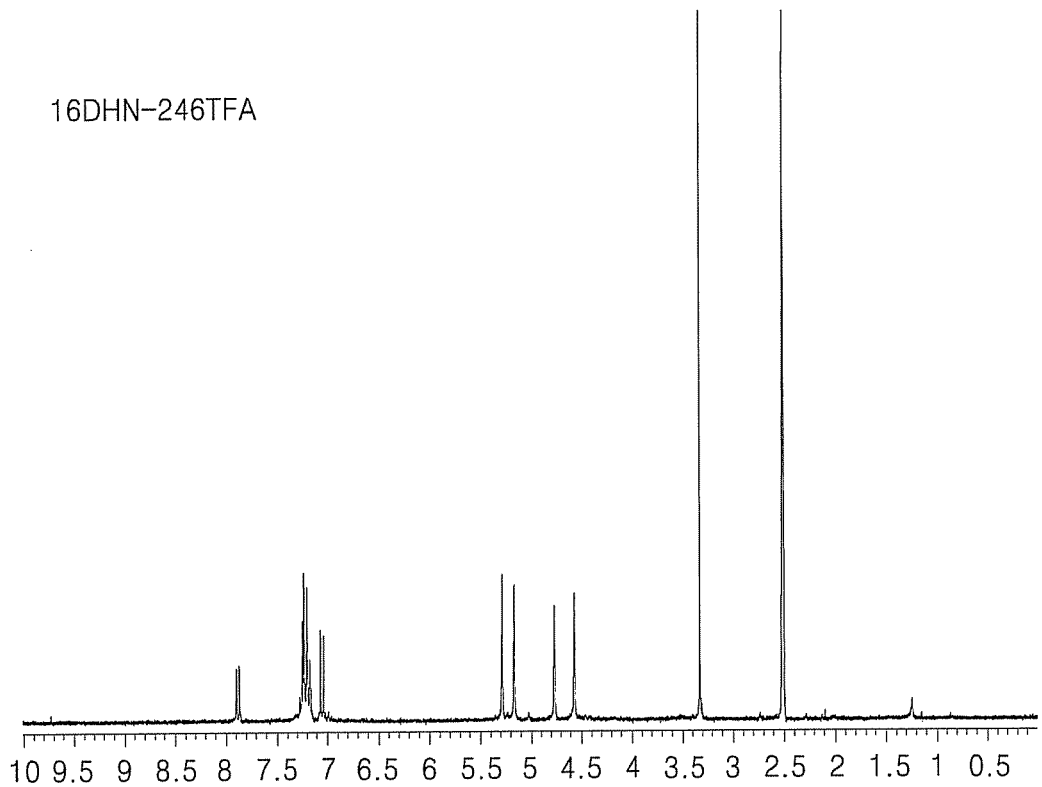

FIG. 7 shows the NMR spectrum of the target material prepared in Synthesis Example 4. The structure of the target material was confirmed by its NMR spectrum as shown in FIG. 7.

Synthesis Example 5

Preparation of 15DHN3AP Represented by Formula 10

A target material was prepared in the same manner as in Synthesis Example 1, except that 3.0 g of 1,5-dihydroxynaphthalene (18.7 mmol), 2.6 g of para-formaldehyde (82.4 mmol), and 3.88 g of 3-aminopyridine (41.2 mmol) were added to a 100 ml one-neck round bottom flask instead of the materials described in Synthesis Example 1.

Figure 8:
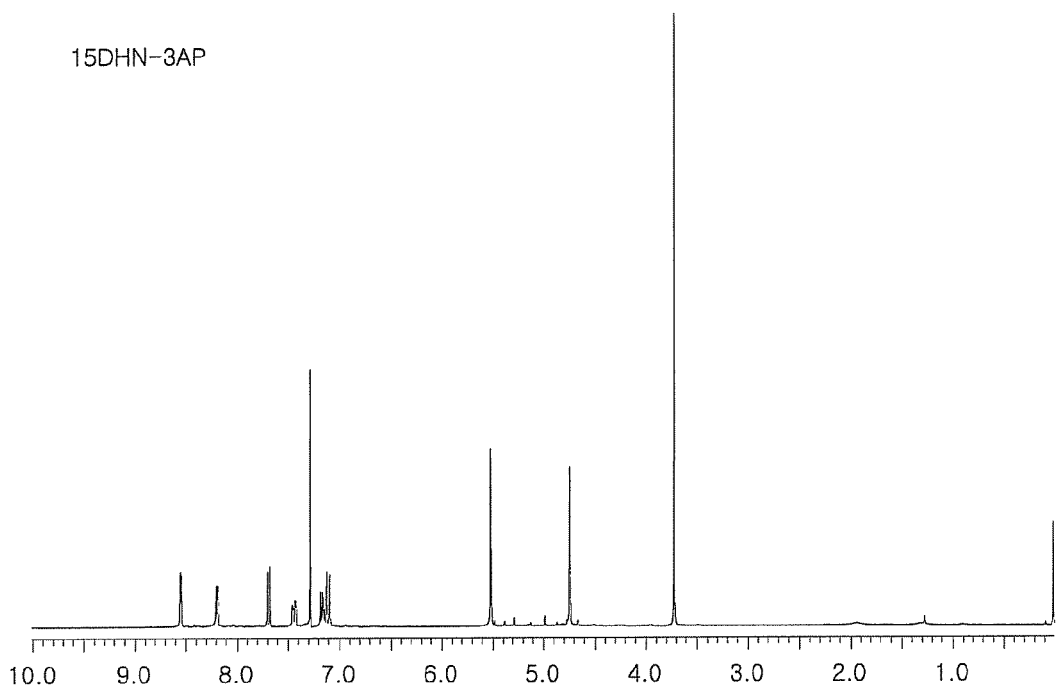

The structure of the target material was confirmed by the nuclear magnetic resonance (NMR) spectrum illustrated in FIG. 8.

Synthesis Example 6

Preparation of 27DHN246TFA Represented by Formula 11

A target material was prepared in the same manner as in Synthesis Example 1, except that 3.0 g of 2,7-dihydroxynaphthalene (18.7 mmol), 2.6 g of para-formaldehyde (82.4 mmol), and 6.06 g of 2,4,6-trifluoroaniline (41.2 mmol) were added to a 100 ml one-neck round bottom flask.

Figure 9:
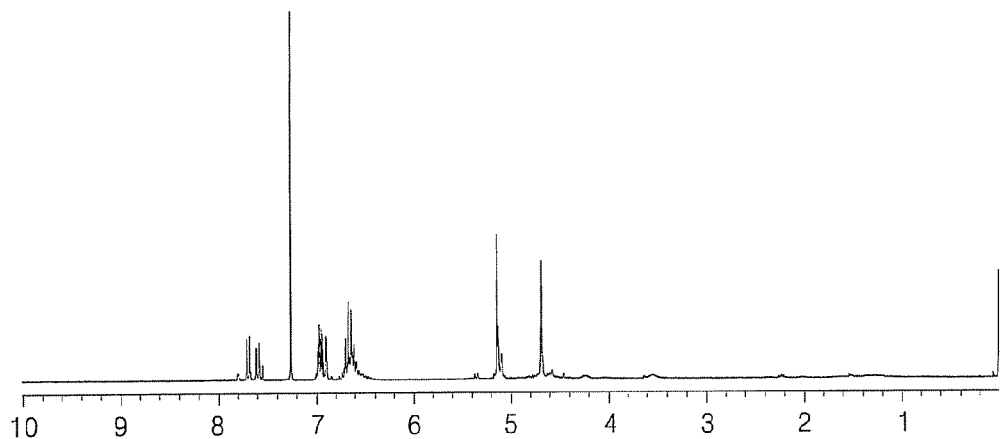

The structure of the target material was confirmed by the NMR spectrum illustrated in FIG. 9.

Reference Example 1

Preparation of t-BuPh-a 15 g of t-butylphenol (0.1 mol), 6.31 g of para-formaldehyde (0.21 mol), and 10.24 g of aniline (0.11 mol) were sequentially added in a 100 ml one-neck round bottom flask, and then mixed in an oil bath at 90° C.

The reaction mixture was opaque in an early stage of the reaction, and about 30 minutes after the reaction, the reaction mixture was converted into a dark brown material in the form of a transparent gel. The reaction mixture was quenched with tetrahydrofurane (THF) to be cooled to room temperature.

The crude product cooled to room temperature was base washed twice by solvent extraction using an aqueous 1N NaOH solution, and then washed once again with deionized water. After the washing process was terminated, an organic layer was dried using $MgSO_4$, and then continuously filtered. The solvent was removed from the filtered solution using a rotary evaporator, and then the purified product was dried in a vacuum oven at 40° C. for 6 hours to obtain t-BuPh-a.

The structure of t-BuPh-a was confirmed by its NMR spectrum.

Thermal stabilities of the compound of Synthesis Example 1, the compound of Synthesis Example 4, and t-BuPh-a of Reference Example 1 were evaluated using thermogravimetric analysis (TGA). FIG. 1 is a graph showing thermogravimetric analysis (TGA) results of the compound prepared in Synthesis Example 1, the compound prepared in Synthesis Example 4, and t-BuPh-a prepared in Reference Example 1. In FIG. 1, thermogravimetric loss was measured at 800° C.

Referring to FIG. 1, it was confirmed that the compound of Formula 6 of Synthesis Example 1 and the compound of Formula 9 of Synthesis Example 4 had less thermogravimetric loss at a temperature of 800° C. or more than did t-BuPh-a. From the result, it can be seen that the compound of Formula 6 and the compound of Formula 9 have excellent thermal stability compared to t-BuPh-a.

Synthesis Example 7

Preparation of Polymer of 16DHN3AP and PBI 65 parts by weight of 16DHN3AP and 35 parts by weight of polybenzimidazole (PBI) were blended together, and the mixture was cured at a temperature in the range of about 180-240° C. to obtain a polymer of 16DHN3AP and PBI.

Synthesis Example 8

Preparation of Polymer of 27DHN34DFA and PBI 65 parts by weight of 27DHN34DFA and 35 parts by weight of polybenzimidazole (PBI) were blended together, and the mixture was cured at a temperature in the range of about 180-240° C. to obtain a polymer of 27DHN34DFA and PBI.

Figure 10:
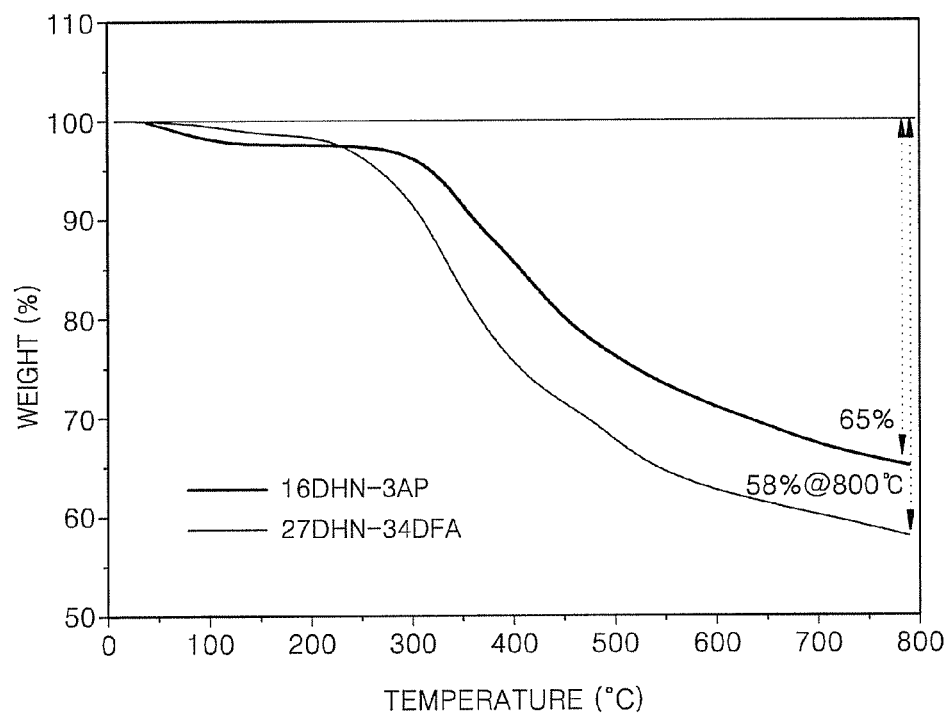
FIGS. 10 and 11 are graphs showing TGA results of 16DHN3AP and 27DHN34DFA and TGA results of a polymer of 16DHN3AP and PBI and a polymer of 27DHN34DFA and PBI prepared in Synthesis Examples 7 and 8, respectively.
Figure 11:
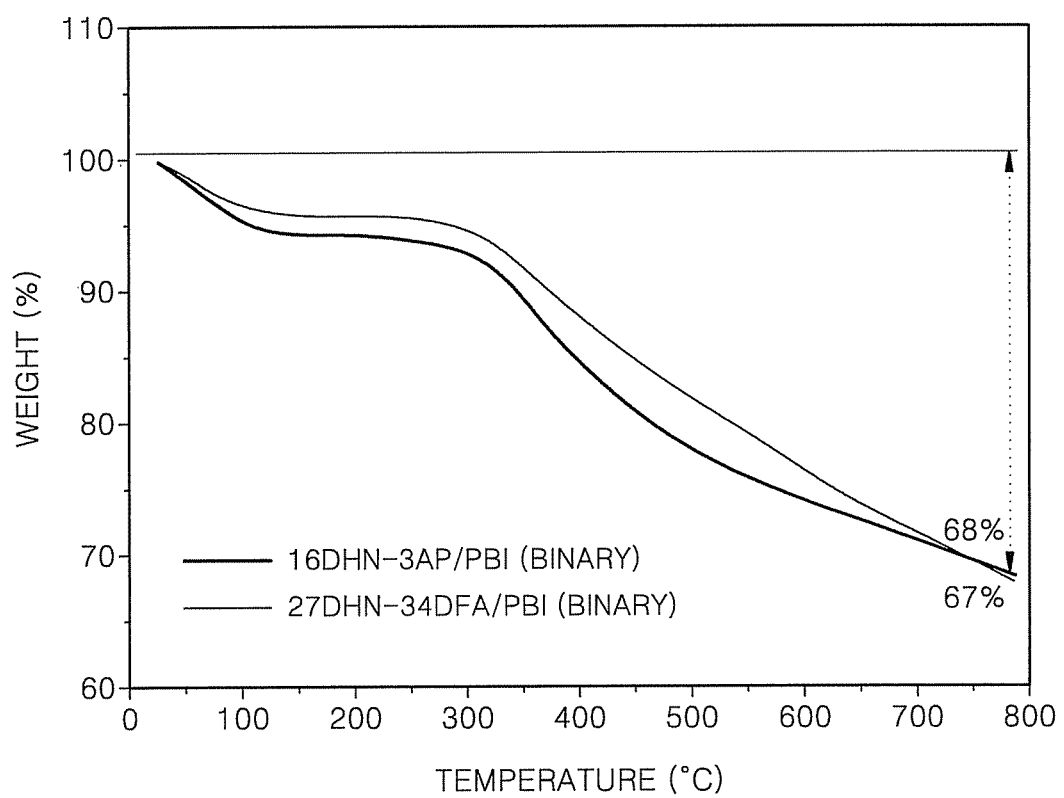

Thermal stabilities of 16DHN3AP, 27DHN34DFA, and the polymer of 16DHN3AP and PBI and the polymer of 27DHN34DFA and PBI that were prepared in Synthesis Examples 7 and 8, were evaluated using thermogravimetric analysis (TGA). The results are respectively shown in FIGS. 10 and 11. In FIGS. 10 and 11, thermogravimetric loss was measured at 800° C.

Referring to FIGS. 10 and 11, it can be seen that 16DHN3AP, 27DHN34DFA, and the polymer of 16DHN3AP and PBI and the polymer of 27DHN34DFA and PBI that were prepared in Synthesis Examples 7 and 8 have excellent thermal stability.

Figure 16:
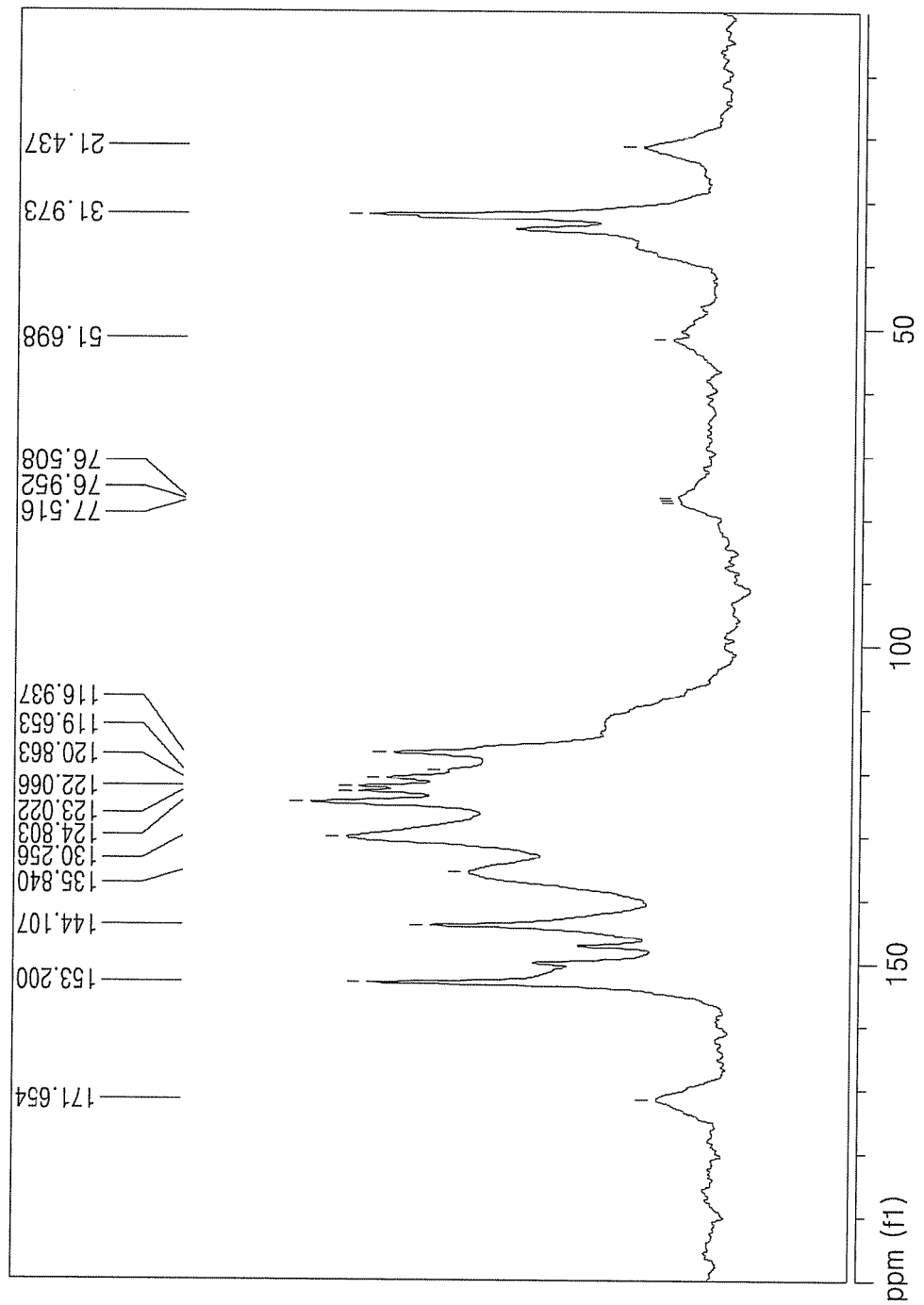
FIG. 16 is a graph showing a solid NMR spectrum of a polymer of 27DHN34DFA and PBI according to an embodiment of the present invention.

The structure of the solid-phase polymer of 27DHN34DFA and PBI was identified by its solid nuclear magnetic resonance (NMR) spectrum as shown in FIG. 16. The NMR spectroscopy was performed using a Varian Unity INOVA600 at 600 MHz.

Example 1

Preparation of Electrode for Fuel Cell and Fuel Cell Including the Electrode 1 g of a catalyst in which 50 wt % of PtCo was supported on carbon and 3 g of NMP were added in a stirrer, and the mixture was stirred using a mortar to prepare a slurry. An NMP solution of 27DHN-34DFA of Formula 7 of Synthesis Example 2 was added to the slurry so that the resultant contained 0.025 g of 27DHN-34DFA. The resultant was further stirred.

Subsequently, an NMP solution of 5 wt % of polyvinylidenefluoride was added to the resultant so that the resultant contained 0.025 g of polyvinylidenefluoride. The resultant was mixed for 10 minutes to prepare a slurry used to form a cathode catalyst layer.

Carbon paper was cut to a size of 4×7 cm$^2$, fixed on a glass plate, and coated by a doctor blade (Sheen instrument). The gap interval was adjusted to 600 μm.

The slurry used to form a cathode catalyst layer was coated onto the carbon paper, and the resultant was dried at room temperature for 1 hour, dried at 80° C. for 1 hour, dried at 120° C. for 30 minutes, and dried at 150° C. for 15 minutes to prepare a cathode (a fuel electrode). The loading amount of PtCo in the prepared cathode was 2.1 mg/cm$^2$.

An electrode prepared by the following processes was used as an anode.

2 g of a catalyst in which 50 wt % of Pt was supported on carbon and 9 g of NMP were added to a stirrer, and the mixture was stirred for 2 minutes using a high speed stirrer.

Subsequently, a solution in which 0.05 g of polyvinylidenefluoride was dissolved in 1 g of NMP was added to the mixture, and the resultant was further stirred for 2 minutes to prepare a slurry used to form an anode catalyst layer. The slurry used to form an anode catalyst layer was coated onto carbon paper coated with a microporous layer using a bar coater. As a result, preparation of the anode was completed. The loading amount of Pt in the prepared anode was 1.3 mg/cm$^2$.

Separately, 60 parts by weight of a benzoxazine-based monomer represented by Formula 12 below, 3 parts by weight of a benzoxazine-based monomer represented by Formula 13 below, and 37 parts by weight of polybenzimidazole were blended together, and then the mixture was cured at about 220° C.

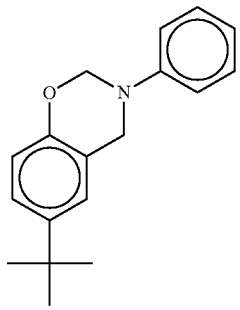

<Formula 12>

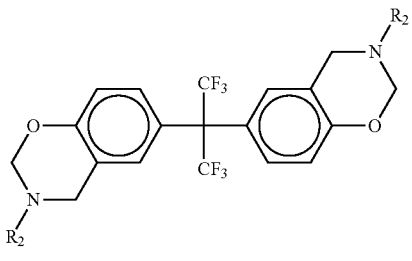

<Formula 13>

R2 = phenyl group

Subsequently, the resultant was impregnated with 85 wt % of phosphoric acid at 80° C. for over 4 hours to form an electrolyte membrane. The amount of phosphoric acid was about 480 parts by weight based on 100 parts by weight of the total weight of the electrolyte membrane.

The electrolyte membrane was disposed between the cathode and the anode to prepare a MEA. The cathode and anode were not impregnated with phosphoric acid.

To prevent gas permeation between the cathode and the anode, a TEFLON membrane for a main gasket with a thickness of 200 μm and a TEFLON membrane for a subgasket with a thickness of 20 μm were joined and disposed between the electrode and the electrolyte membrane. The pressure applied to the MEA was adjusted to 1, 2, 3 N-m torque step by step using a wrench to assemble a cell.

Electricity was generated by causing hydrogen to flow into the anode (flowrate: 100 ccm) and causing air to flow into the cathode (flowrate: 250 ccm) at 150° C. under a condition in which the electrolyte membrane was not humidified. Properties of the fuel cell prepared were measured. An electrolyte doped with a phosphoric acid was used, and thus the performance of the fuel cell improved as time elapsed. Aging was performed until an operating voltage reached a peak, and then the properties of the fuel cell were finally evaluated. In addition, the area of the cathode and anode was fixed to a size of 2.8×2.8 (7.84 cm$^2$), and the thickness of the cathode was about 430 μm and the thickness of the anode was about 390 μm, although the thicknesses of the cathode and the anode may have varied according to the distribution of the carbon paper.

Example 2

Preparation of Electrode for Fuel Cell and Fuel Cell Including the Electrode A cathode was prepared in the same manner as in Example 1, except that 16DHN-3AP of Formula 6 of Synthesis Example 1 was used instead of 27DHN-34DFA of Formula 7 of Synthesis Example 2, and a fuel cell using the cathode was prepared.

Examples 3-5

Preparation of Electrode for Fuel Cell and Fuel Cell Including the Electrode Cathodes were prepared in the same manner as in Example 1, except that 27DHN-2AP of Formula 8 of Synthesis Example 3, 16DHN246TFA of Formula 9 of Synthesis Example 4, and 15DHN3AP of Formula 10 of Synthesis Example 5, respectively were used instead of 27DHN- 34DFA of Formula 7 of Synthesis Example 2, and fuel cells using the cathodes were prepared.

Comparative Example 1

Preparation of Electrode for Fuel Cell and Fuel Cell Including the Electrode

A cathode was prepared in the same manner as in Example 1, except that 27DHN-34DFA of Formula 7 of Synthesis Example 2 was not used, and a fuel cell using the cathode was prepared.

Figure 2:
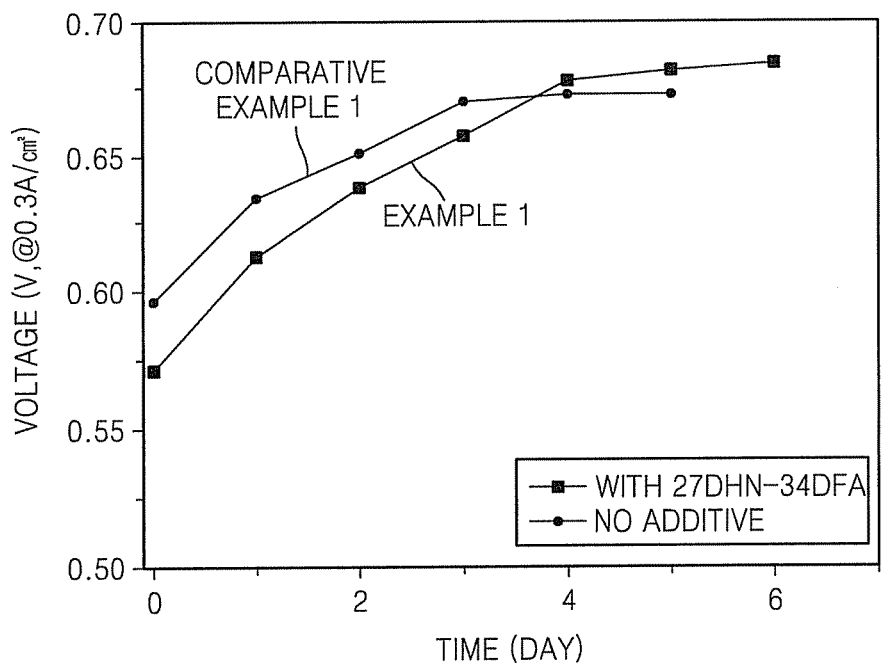
FIG. 2 is a graph showing a change in voltage with respect to time of fuel cells prepared in Example 1 and Comparative Example 1.

FIG. 2 is a graph showing a change in voltage with respect to time of fuel cells prepared in Example 1 and Comparative Example 1.

Referring to FIG. 2, although the fuel cell of Example 1 had low initial performance, it had improved voltage performance by faster activation compared to the fuel cell of Comparative Example 1.

Figure 3:
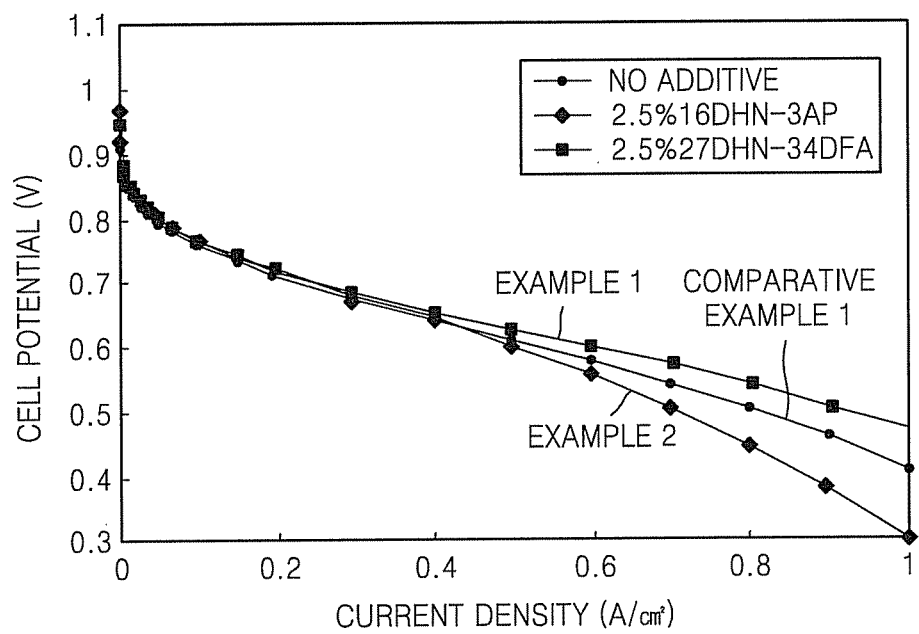
FIG. 3 is a graph showing a change in cell potential with respect to current density of fuel cells prepared in Examples 1 and 2 and Comparative Example 1.

In addition, changes in cell potential with respect to current density of the fuel cells of Examples 1 and 2 and Comparative Example 1 were measured, and the results are shown in FIG. 3.

Referring to FIG. 3, the fuel cells of Examples 1 and 2 had higher cell voltage characteristics compared to the fuel cell of Comparative Example 1.

Cell performances of the fuel cells of Examples 1 through 5 and Comparative Example 1 were measured, and the results are shown in Table 1 below.

TABLE 1

|  | Voltage at 0.3 A/cm$^2$ (V) | Tafel slope (mV/dec) |
|---|---|---|
| 27DHN-34DFA (Example 1) | 0.685 | 98 |
| 16DHN-3AP (Example 2) | 0.685 | 99 |
| 27DHN-2AP (Example 3) | 0.686 | 104 |
| 16DHN246TFA (Example 4) | 0.688 | 104 |
| 15DHN3AP (Example 5) | 0.684 | 108 |
| Comparative Example 1 | 0.678 | 97 |

Referring to Table 1, the fuel cells of Examples 1 through 5 have a higher Tafel slope and improved voltage characteristics compared to the fuel cell of Comparative Example 1.

Example 6

Preparation of an Electrolyte Membrane for a Fuel Cell and a Fuel Cell Using the Electrolyte Membrane 1 g of a catalyst in which 50% by weight of PtCo was loaded on carbon and 3 g of NMP as a solvent were added to a stirrer, and the mixture was agitated using a mortar to prepare a slurry.

Then, a solution of 5% by weight of polyvinylidenefluoride and NMP was added to the mixture to set the amount of the polyvinylidenefluoride to 0.025 g, and the mixture was mixed for 10 minutes to prepare a slurry for a cathode catalyst layer.

Carbon paper was cut into pieces of 4×7 cm$^2$ in size, and the pieces were fixed on a glass plate and coated using a doctor blade (Sheen instrument), wherein the gap interval of the doctor blade was 600 μm.

The slurry for a cathode catalyst layer was coated onto the carbon paper and dried at room temperature for 1 hour, at 80° C. for 1 hour, at 120° C. for 30 minutes and at 150° C. for 15 minutes to prepare a cathode (a fuel electrode). The amount of loaded Pt/Co in the prepared cathode was 2.32 mg/cm$^2$.

An electrode prepared according to the process as follows was used as an anode.

2 g of a catalyst in which 50% by weight of Pt is supported on carbon and 9 g of NMP solvent were added to a stirrer and the mixture was agitated in a high-speed agitator for 2 minutes.

Then, a solution of 0.05 g of polyvinylidenefluoride dissolved in 1 g of NMP was added thereto and agitated for 2 minutes to prepare a slurry for an anode catalyst layer. The slurry was coated onto carbon paper on which microporous layer was coated using a bar coater. The amount of loaded Pt in the prepared anode was 1.44 mg/cm$^2$.

Separately, 65 parts by weight of 27DHN-34DFA of Formula 7 prepared in Synthesis Example 2 was blended with 35 parts by weight of polybenzimidazole (PBI), and the mixture was cured at about 220° C.

Then, the resultant was impregnated with 85% by weight of phosphoric acid at 80° C. for more than 4 hours to prepare an electrolyte membrane. The amount of phosphoric acid was about 530 parts by weight based on 100 parts by weight of electrolyte membrane.

A membrane electrode assembly (MEA) was prepared by interposing the electrolyte membrane between the cathode and the anode. The cathode and anode were not impregnated with phosphoric acid.

A 200 μm TEFLON membrane for a main gasket and a 20 μm TEFLON membrane for a sub gasket were overlapped on an interface between the electrodes and electrolyte membrane in order to prevent gas permeation between the cathode and the anode. The pressure applied to the MEA was adjusted to 1, 2, 3 N-m torque step by step using a wrench to assemble a cell.

Characteristics of fuel cells were measured while operating by supplying hydrogen to the anode at 100 ccm and supplying air to the cathode at 250 ccm at 150° C. while the electrolyte membrane was not hydrated. Since cell efficiency increases with time by using the electrolyte doped with phosphoric acid, the final efficiency was measured after the fuel cell was aged until operational voltage was maximized. The area of the cathode and the anode was fixed to 2.8×2.8=7.84 cm$^2$, and the thickness of the cathode was about 430 μm and the thickness of the anode was about 390 μm although the thicknesses of the cathode and the anode may have varied according to the distribution of the carbon paper.

Examples 7 to 9

Preparation of an Electrolyte Membrane for a Fuel Cell and a Fuel Cell Using the Electrolyte Membrane An electrolyte membrane and a fuel cell were prepared in the same manner as in Example 6, except that 27DHN-246DFA, 16DHN-34DFA, and 16DHN-3AP were respectively used instead of 27DHN-34DFA of Formula 7 prepared in Synthesis Example 2.

Figure 12:
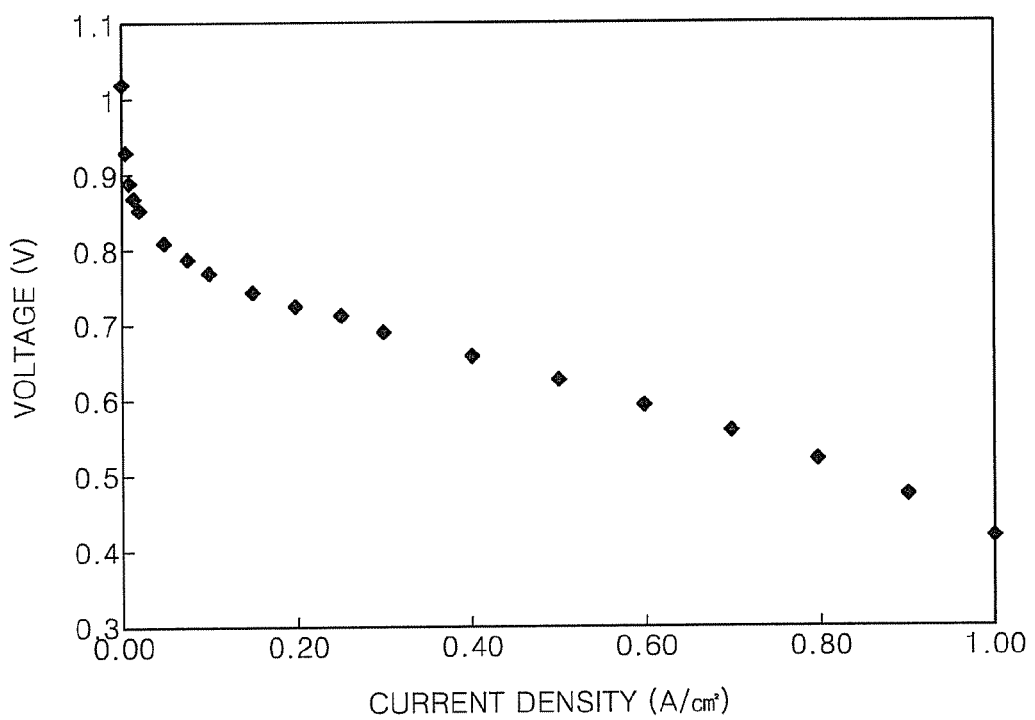
FIG. 12 is a graph showing voltage characteristics according to current density of a fuel cell prepared in Example 6.

Voltage characteristics according to current density of the fuel cell prepared in Example 6 were measured, and the results are shown in FIG. 12. In FIG. 12, "OCV" denotes an open circuit voltage, and "0.2 A/cm$^2$" denotes cell voltage at a current density of 0.2 A/cm$^2$.

Referring to FIG. 12, the fuel cell of Example 6 had an open circuit voltage of more than 1 V and 0.72 V at 0.2 A/cm$^2$.

Figure 13:
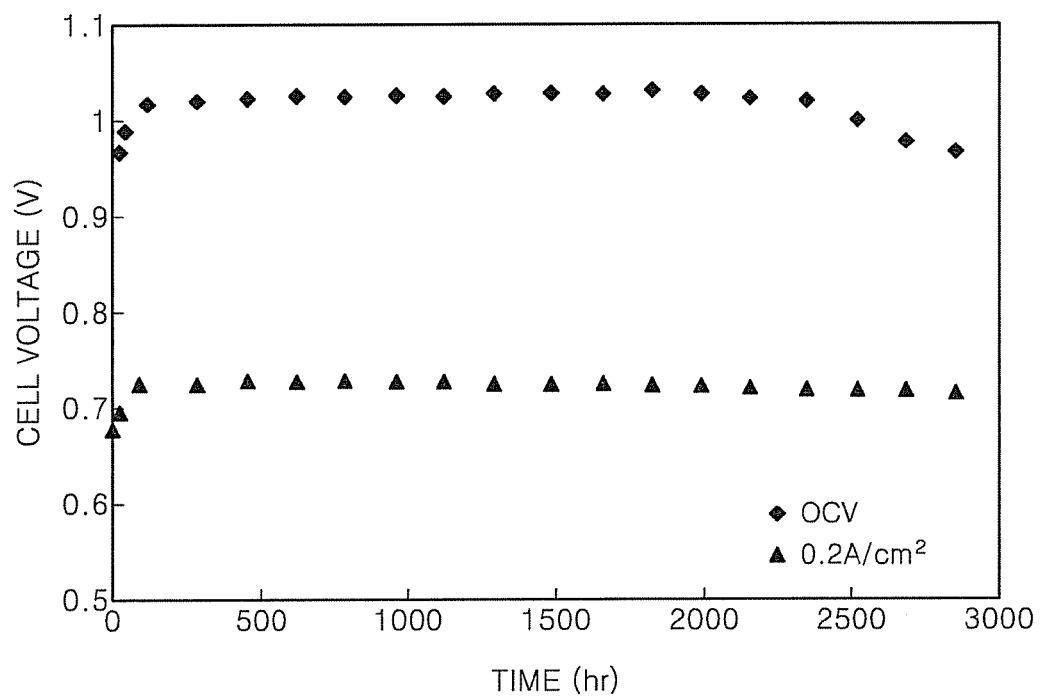
FIG. 13 is a graph showing a change in cell voltage according to time of a fuel cell prepared in Example 6.

In addition, a change in cell voltage according to time was measured, and the results are shown in FIG. 13.

Referring to FIG. 13, the fuel cell of Example 6 showed excellent cell voltage characteristics.

Figure 14:
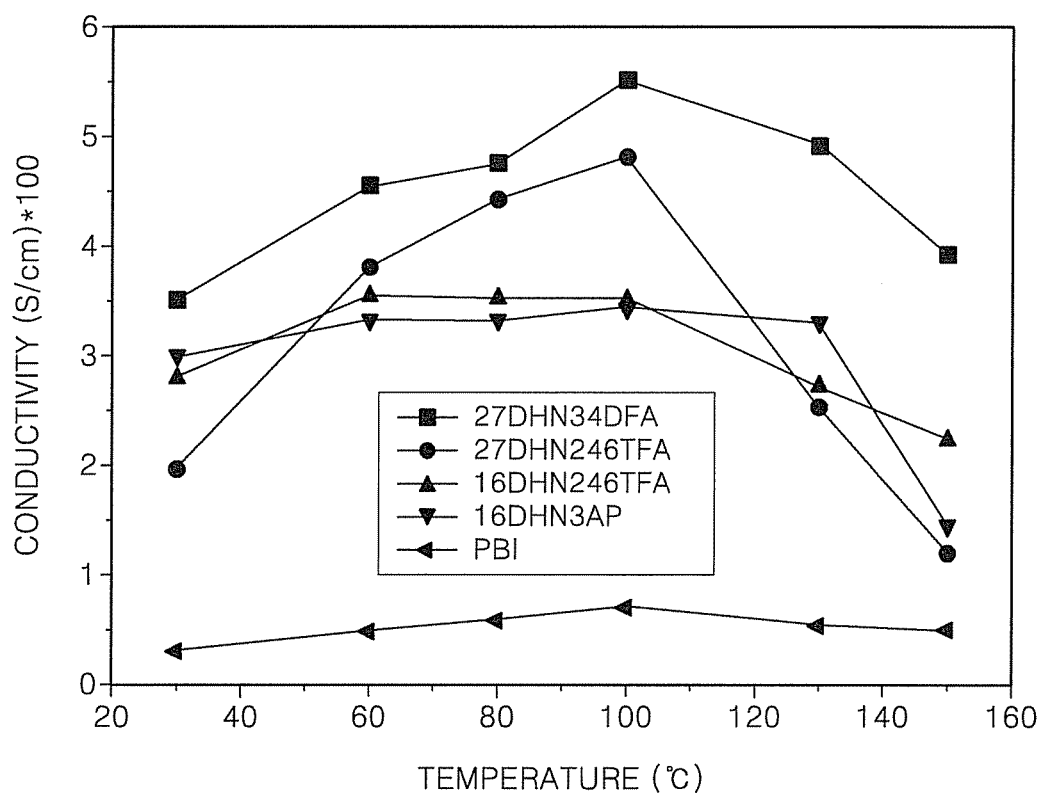
FIGS. 14 and 15 are graphs respectively showing conductivity according to temperature and phosphoric acid doping level of electrolyte membranes prepared in Examples 6 through 9.
Figure 15:
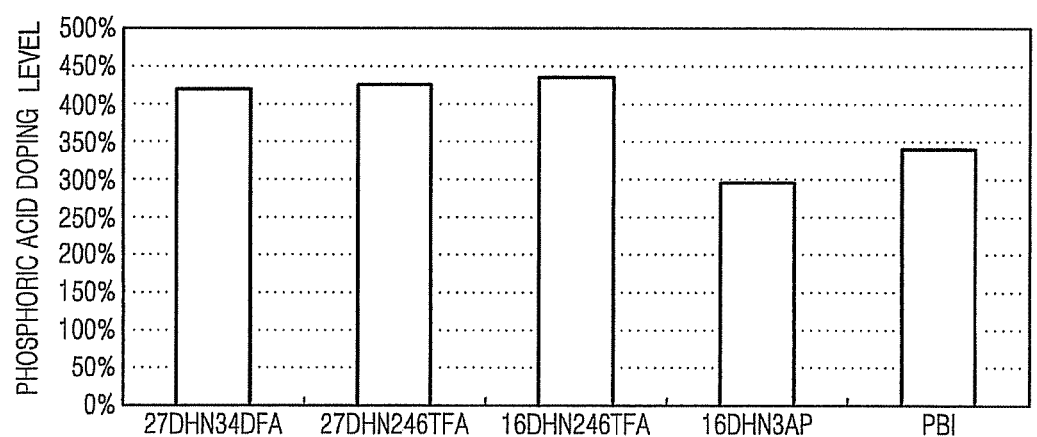

Conductivity according to temperature and phosphoric acid doping level of the electrolyte membranes prepared in Examples 6 through 9 was measured, and the results are shown in FIGS. 14 and 15.

Referring to FIGS. 14 and 15, the electrolyte membranes of Examples 6 through 9 showed higher conductivity compared with the PBI electrolyte membrane, and showed good durability due to a small doping amount of phosphoric acid.

In FIG. 15, the doping level is shown as a percentage based on the weight of the impregnated amount.

Example 10

Preparation of a Fuel Cell

A fuel cell was prepared in the same manner as in Example 6, except that the slurry for a cathode catalyst layer was prepared in the following processes.

1 g of a catalyst in which 50% by weight of PtCo was loaded on carbon and 3 g of NMP as a solvent were added to a stirrer, and the mixture was agitated using a mortar to prepare a slurry. An NMP solution of 27DHN-34DFA of Formula 7 prepared in Synthesis Example 2 was then added to the slurry so that the resultant contained 0.025 g of 27DHN-34DFA. The resultant was further stirred.

Then, a solution of 5% by weight of polyvinylidenefluoride and NMP was added to the mixture to set the amount of the polyvinylidenefluoride to 0.025 g, and the mixture was mixed for 10 minutes to prepare a slurry for a cathode catalyst layer.

Comparative Example 2

Preparation of Fuel Cell

A fuel cell was prepared in the same manner as in Example 10, except that 27DHN-34DFA of Formula 7 was not used in the preparation of the cathode and a polybenzimidazole (PBI) membrane was used as an electrolyte membrane.

Figure 17:
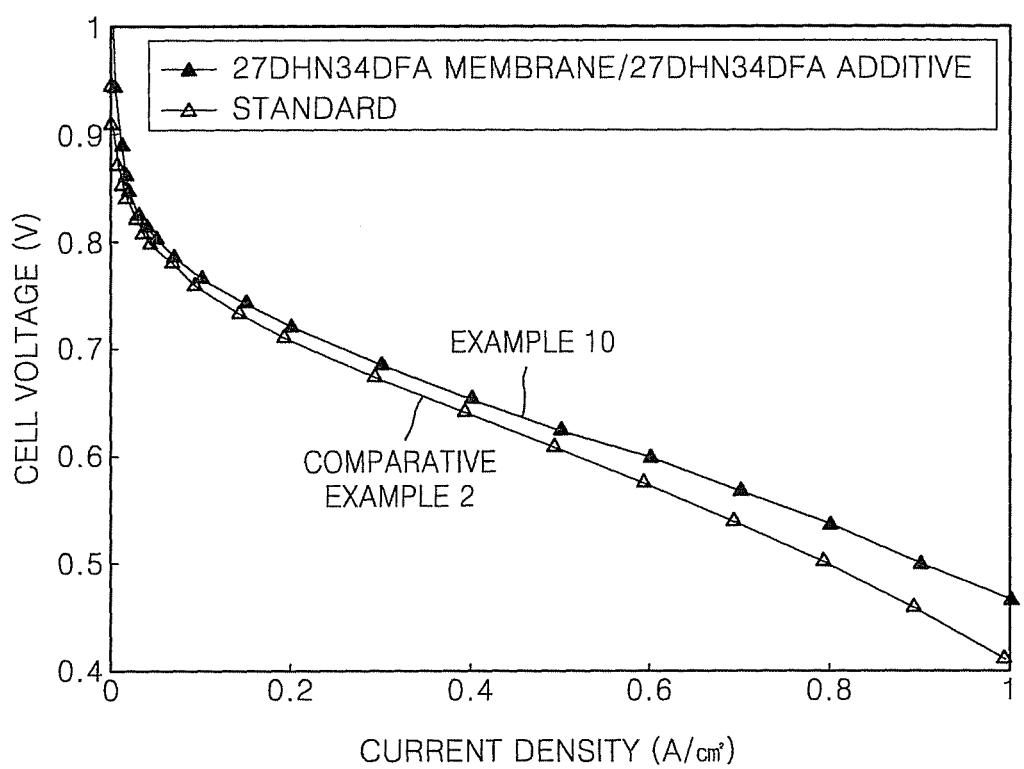
FIG. 17 is a graph showing cell voltage characteristics according to current density of fuel cells prepared in Example 10 and Comparative Example 2.

Cell voltage characteristics with respect to current density of the fuel cells prepared in Example 10 and Comparative Example 2 were measured, and the results are shown in FIG. 17.

Referring to FIG. 17, performance of the MEA prepared in Example 10 was improved compared with that of the MEA prepared in Comparative Example 2.

While aspects of the present invention have been particularly shown and described with reference to differing embodiments thereof, it should be understood that these exemplary embodiments should be considered in a descriptive sense only and not for purposes of limitation. Descriptions of features or aspects within each embodiment should typically be considered as available for other similar features or aspects in the remaining embodiments.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An electrode for a fuel cell comprising a catalyst layer, wherein the catalyst layer comprises a catalyst and a polymer that is a polymerization product of the naphthoxazine-based monomer selected from compounds represented by Formulae 3 through 5 below or a polymerization product of the naphthoxazine-based monomer selected from compounds represented by Formulae 3 through 5 below and a crosslinkable compound

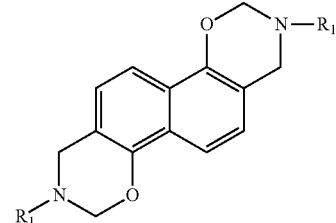
<Formula 3>

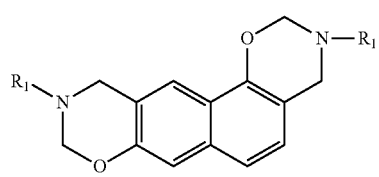
<Formula 4>

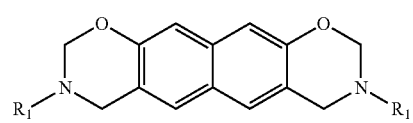
<Formula 5> wherein $R_1$ is one selected from groups represented by the following formulae:

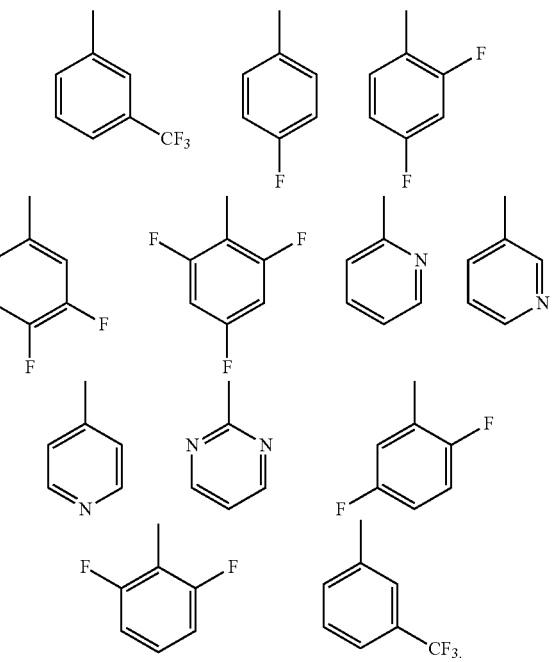

2. The electrode of claim 1, wherein the amount of the polymer is in the range of 0.1 to 65 parts by weight based on 100 parts by weight of the catalyst.

3. The electrode of claim 2, wherein the catalyst is:
   Pt;
   a metal-Pt alloy including Pt and at least one metal selected from the group consisting of Au, Pd, Rh, Ir, Ru, Sn, Mo, Co, and Cr; or a mixture including Pt and at least one metal selected from the group consisting of Au, Pd, Rh, Ir, Ru, Sn, Mo, Co, and Cr.

4. The electrode of claim 1, wherein the catalyst is a catalyst metal or a support catalyst comprising a catalyst metal loaded on a carbonaceous support, wherein the catalyst metal is:

Pt;

a metal-Pt alloy including Pt and at least one metal selected from the group consisting of Au, Pd, Rh, Ir, Ru, Sn, Mo, Co, and Cr; or a mixture including Pt and at least one metal selected from the group consisting of Au, Pd, Rh, Ir, Ru, Sn, Mo, Co, and Cr.

5. The electrode of claim 1, wherein the catalyst layer comprises at least one proton conductor selected from the group consisting of a phosphoric acid and a $C_1$-$C_{20}$ organic phosphonic acid.

6. The electrode of claim 1, further comprising at least one binder selected from the group consisting of poly(vinylidene fluoride), polytetrafluoroethylene (PTFE), a tetrafluoroethylene-hexafluoropropylene copolymer, fluorinated ethylene propylene (FEP), styrene butadiene rubber (SBR), and polyurethane.

7. The electrode of claim 1, wherein the catalyst layer comprises a catalyst and a binder, wherein the binder is at least one selected from the group consisting of poly(vinylidene fluoride), polytetrafluoroethylene (PTFE), a tetrafluoroethylene-hexafluoropropylene copolymer, fluorinated ethylene propylene (FEP), styrene butadiene rubber (SBR), and polyurethane, and the amount of the binder is in the range of 0.1 to 50 parts by weight based on 100 parts by weight of the catalyst.

8. The electrode of claim 1, wherein the naphthoxazine-based monomer is selected from compounds represented by Formulae 6 through 11 below:

<Formula 6>

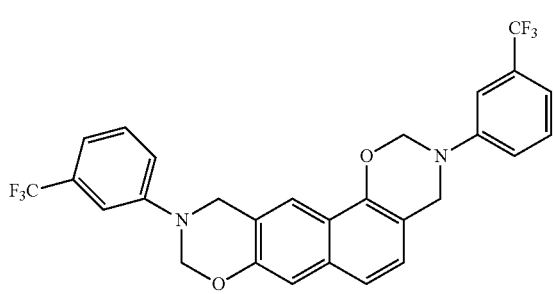

<Formula 7>

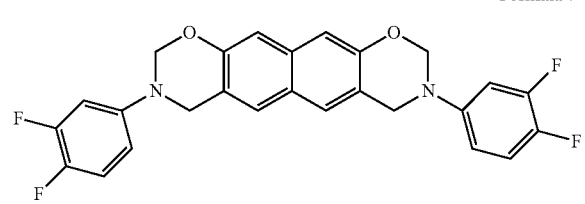

<Formula 8>

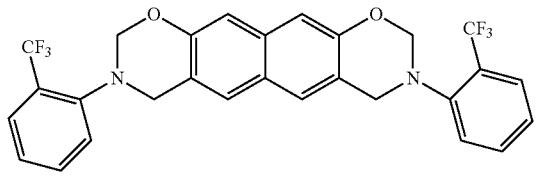

<Formula 9>

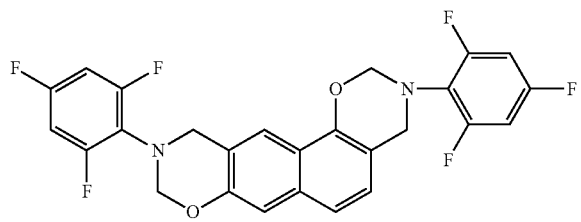

<Formula 10>

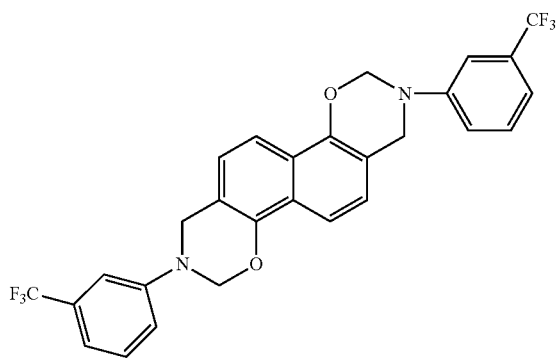

<Formula 11>

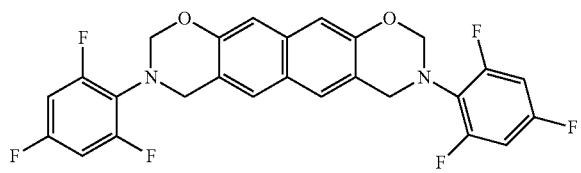

9. The electrode of claim 1, wherein the crosslinkable compound is at least one compound selected from the group consisting of polybenzimidazole, a polybenzimidazole-base complex, polybenzthiazole, polybenzoxazole, and polyimide.

10. A fuel cell comprising: a cathode; an anode; and an electrolyte membrane interposed between the cathode and the anode, wherein at least one of the cathode and the anode comprises the electrode of claim 1.

11. The fuel cell of claim 10, wherein the electrolyte membrane comprises a polymer that is a polymerization product of the naphthoxazine-based monomer selected from compounds represented by Formulae 3 through 5 below or a polymerization product of the naphthoxazine-based monomer selected from compounds represented by Formulae 3-5 below and a crosslinkable compound:

<Formula 3>
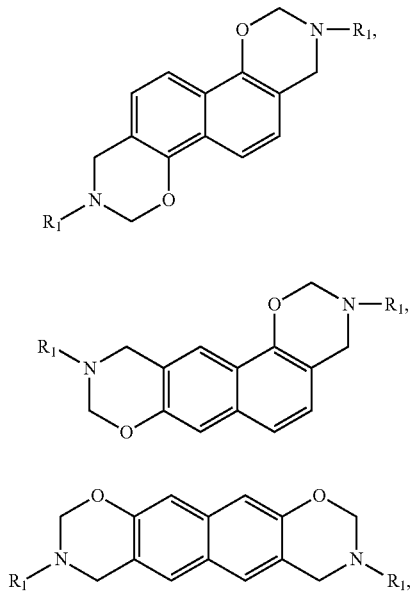
<Formula 4>
and
<Formula 5>
wherein R₁ is one selected from groups represented by the following formulae:
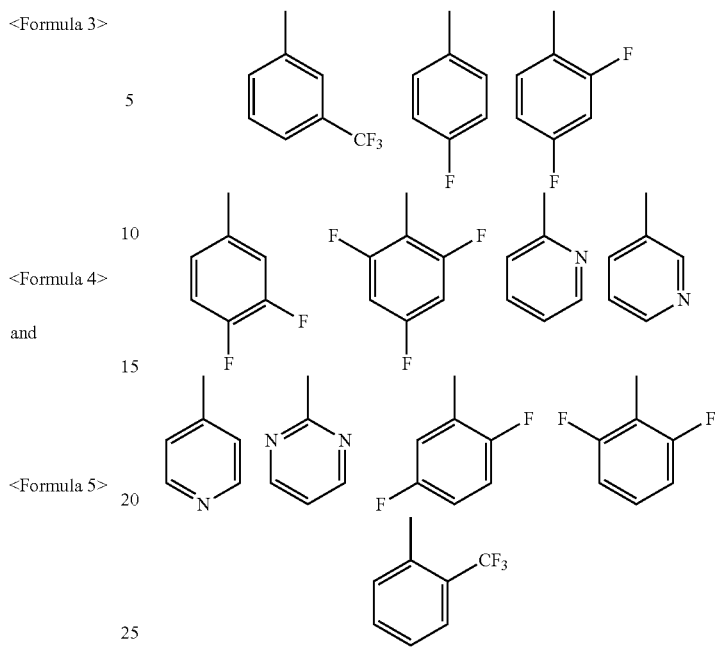
* * * * *